United States Patent [19]

Koch

[11] Patent Number: 5,061,285
[45] Date of Patent: Oct. 29, 1991

[54] ENOSSAL IMPLANT AND PROCESS FOR INSERTING ENOSSAL IMPLANT INTO THE JAWBONE

[75] Inventor: Werner-Lutz Koch, Liebenau/Hanover, Fed. Rep. of Germany

[73] Assignee: Implanto-Lock Gesellschaft mit beschränkter Haftung für Implantatforschung-und Entwicklung

[21] Appl. No.: 520,120

[22] Filed: May 8, 1990

Related U.S. Application Data

[60] Continuation of Ser. No. 95,844, Sep. 10, 1989, abandoned, which is a division of Ser. No. 795,650, Nov. 6, 1985, Pat. No. 4,731,085.

[30] Foreign Application Priority Data

Nov. 9, 1984 [DE] Fed. Rep. of Germany ....... 3440952
Apr. 26, 1985 [DE] Fed. Rep. of Germany ....... 3515154
Sep. 10, 1985 [DE] Fed. Rep. of Germany ....... 3532125
Nov. 4, 1985 [EP] European Pat. Off. ........ 85113975.8

[51] Int. Cl.$^5$ ............................................... A61F 2/28
[52] U.S. Cl. ....................................... 623/16; 433/173
[58] Field of Search ....................... 623/16, 18, 23, 66; 433/173, 174, 175, 176, 177, 178

[56] References Cited

U.S. PATENT DOCUMENTS

3,863,344 2/1975 Pillet ................................. 433/173
4,552,532 11/1985 Mozsary ......................... 433/174 X
4,731,085 3/1988 Koch .................................... 623/16

Primary Examiner—David J. Isabella
Assistant Examiner—D. S. Brittingham
Attorney, Agent, or Firm—Toren, McGeady & Associates

[57] ABSTRACT

The invention relates to an enossal implant, which comprises a primary cylinder (10) with a central longitudenal bore (13) which can be introduced into the jawbone and is anchored therein in positive and/or non-positive manner, as well as a secondary cylinder (100) insertable into the primary cylinder (10) and which has an oscillating rod (211) inserted and held in the longitudenal bore (13) and guide tube (30) of primary cylinder (10), said rod carrying an upper modular tube (220) made from an elastic material arranged at a distance from guide tube (30), accompanied by the formation of an air gap (225) and which is constructed at its free upper end for the connection of the dental prosthesis, whereas its lower end is connected in fixed or detachable manner to the primary cylinder (10), so that an implant is obtained which not only leads to a positive and nonpositive connection to the bone and a load-free stabilization of the primary cylinder (10), but whose oscillating rod (211) absorbs the horizontal, vertical and torsional forces occuring in the mouth and diverts same into the bottom of the implant (FIG. 12).

44 Claims, 13 Drawing Sheets

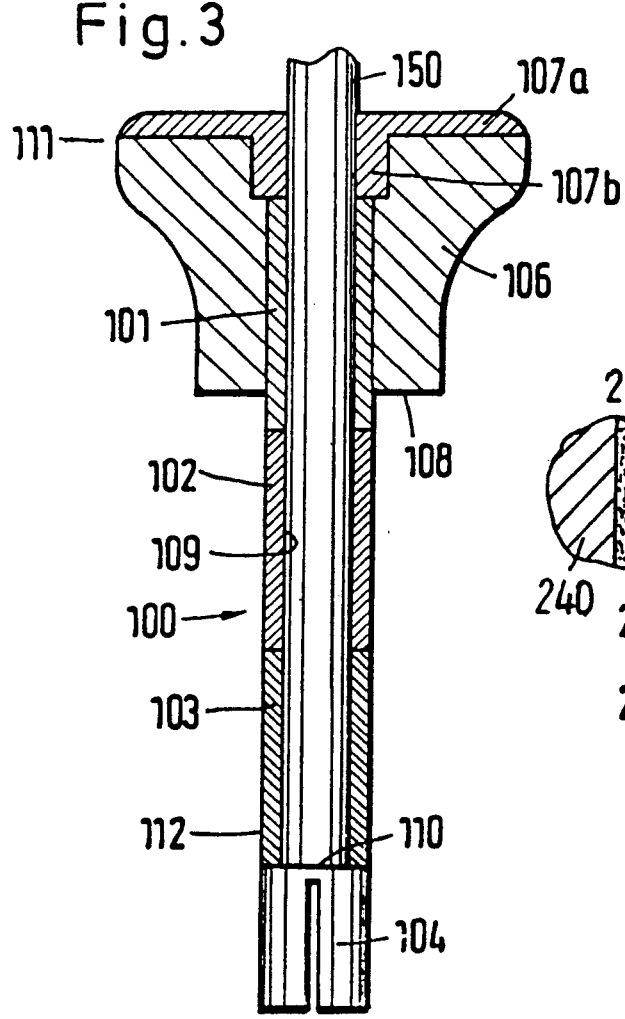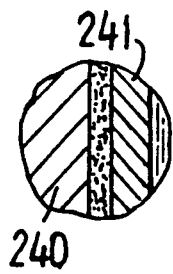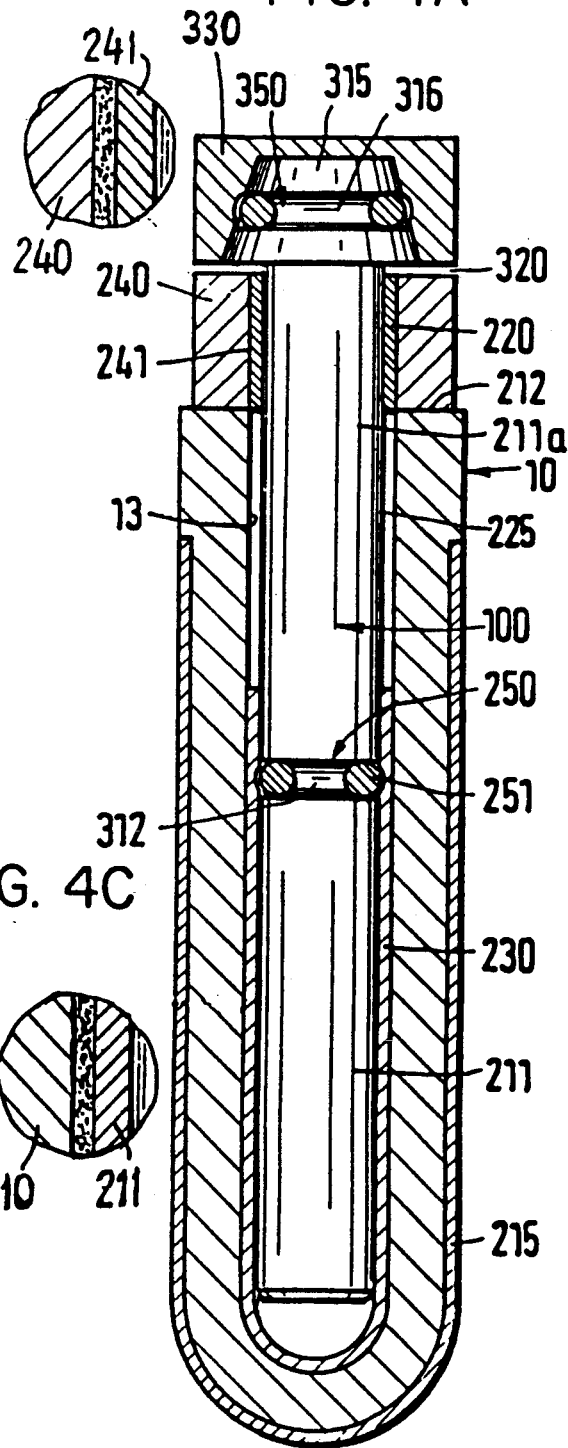

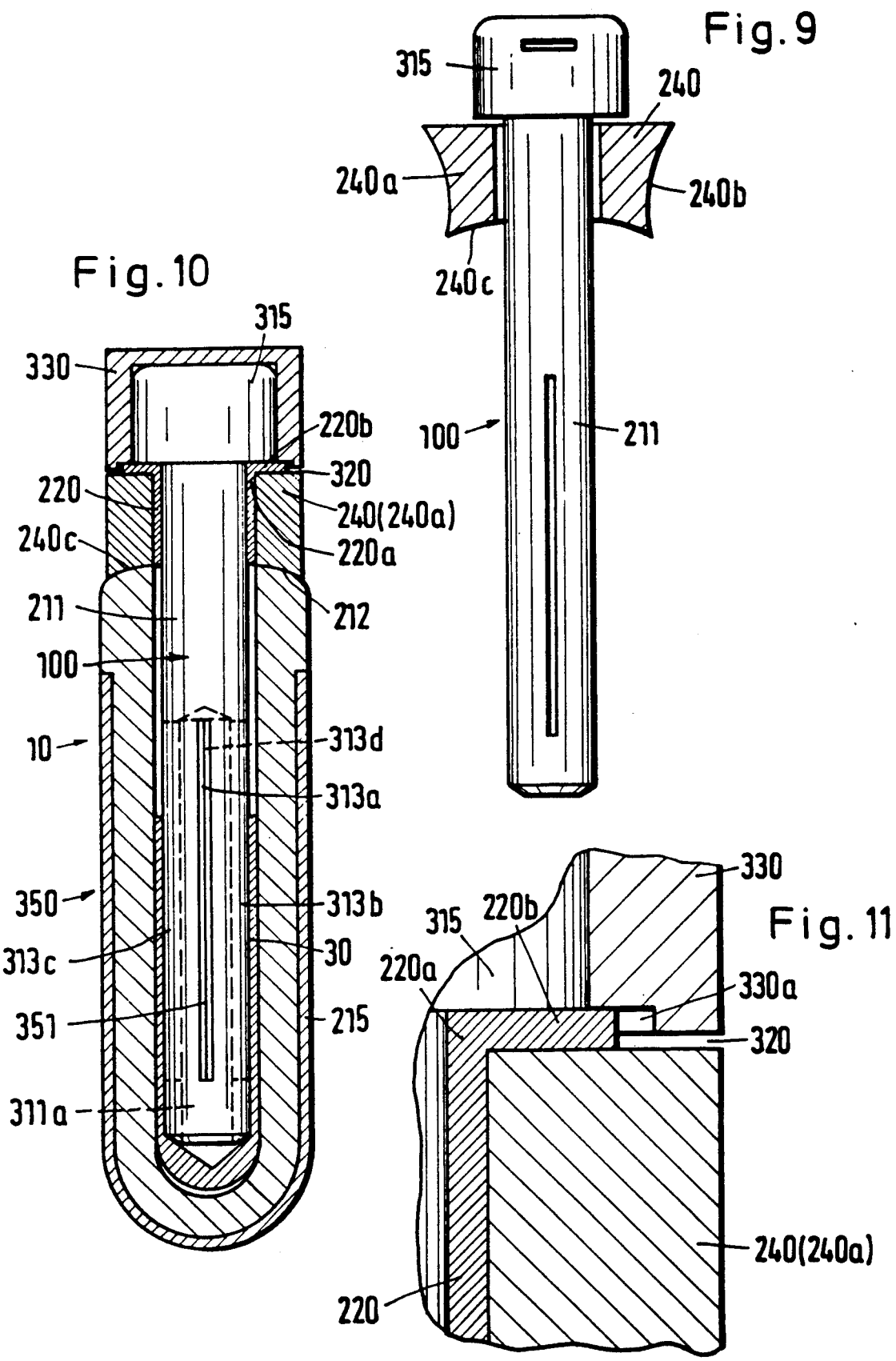

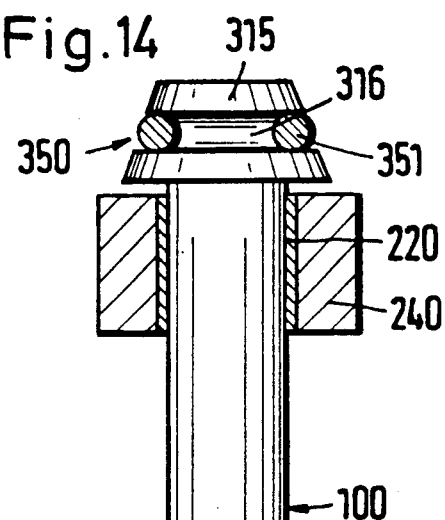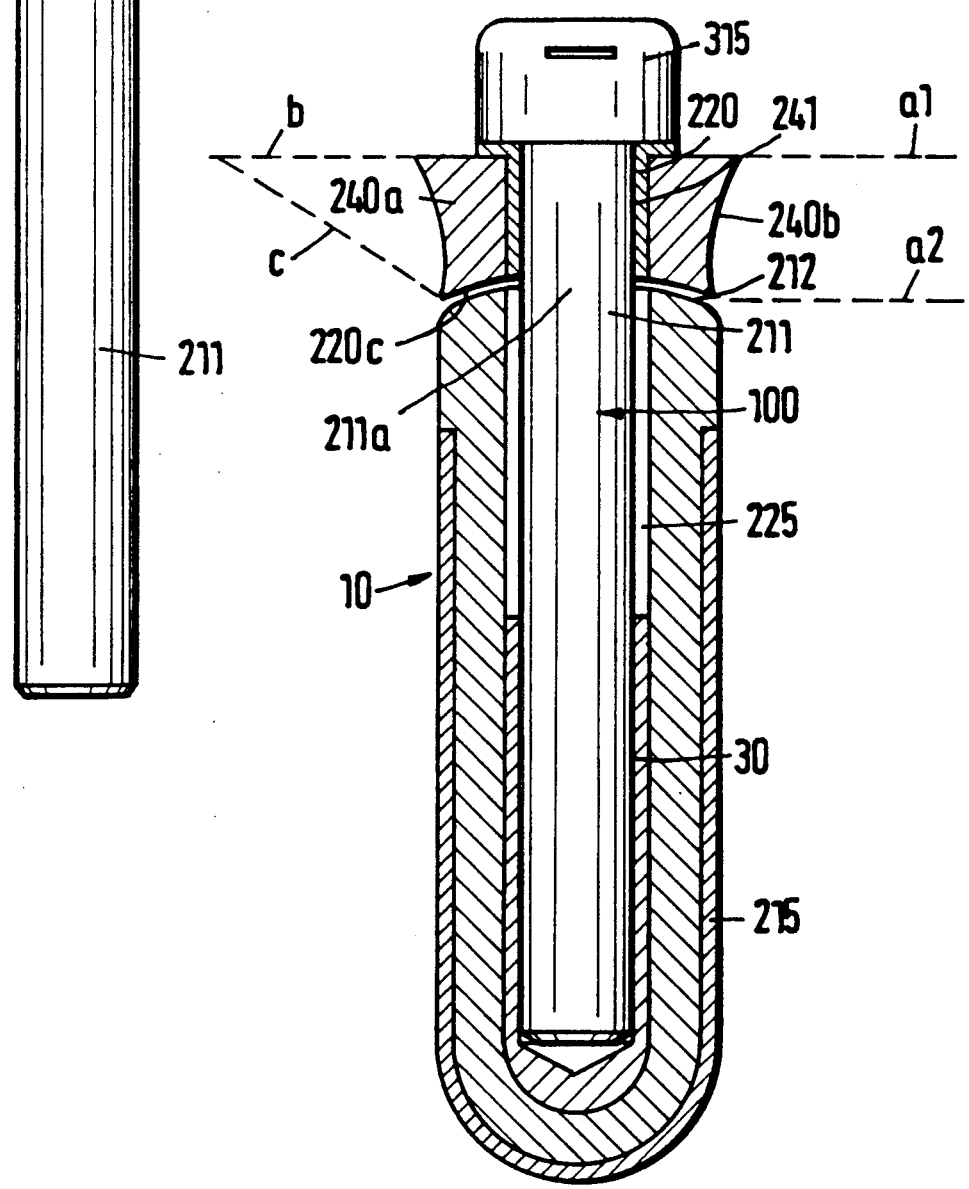

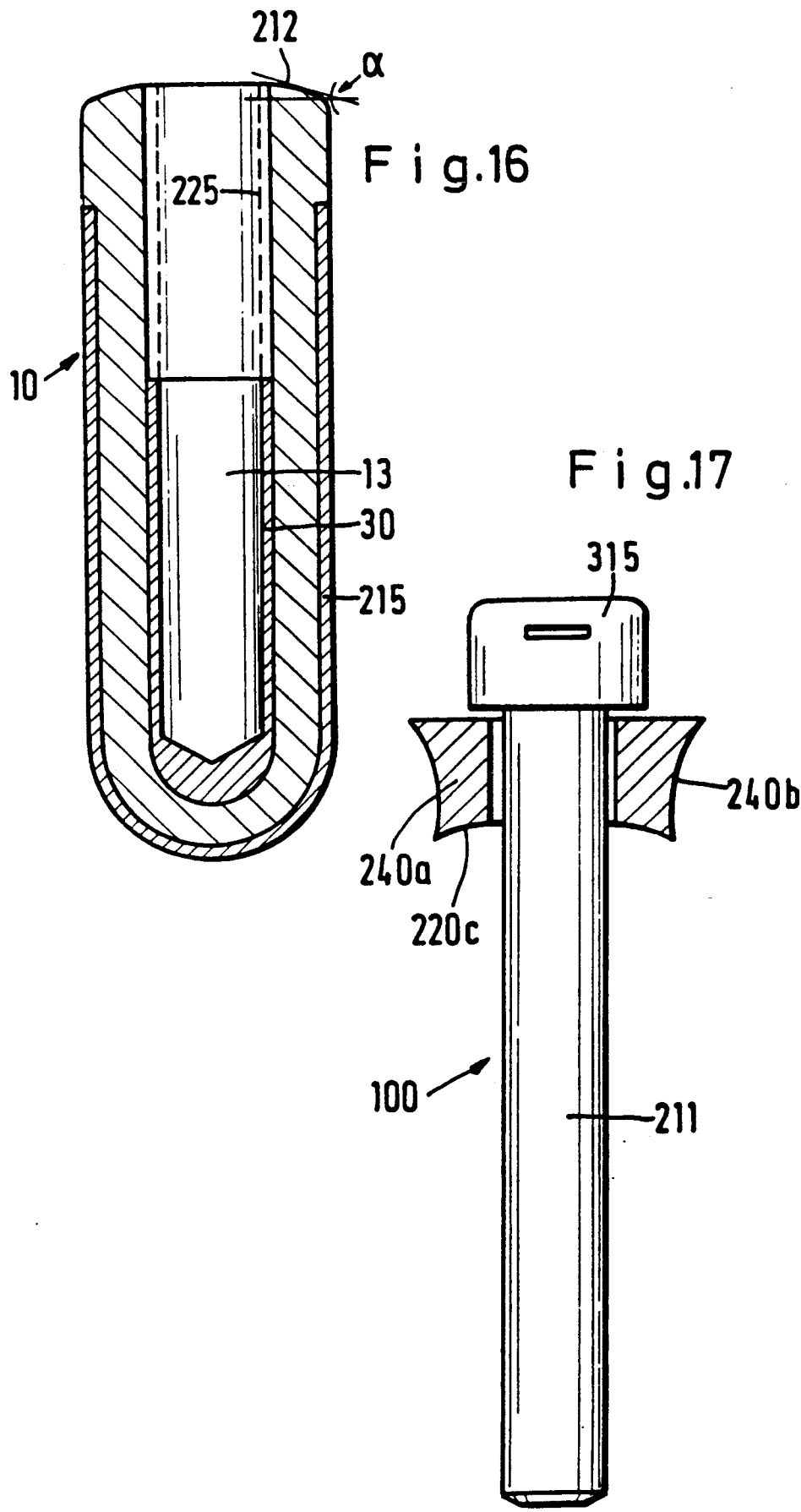

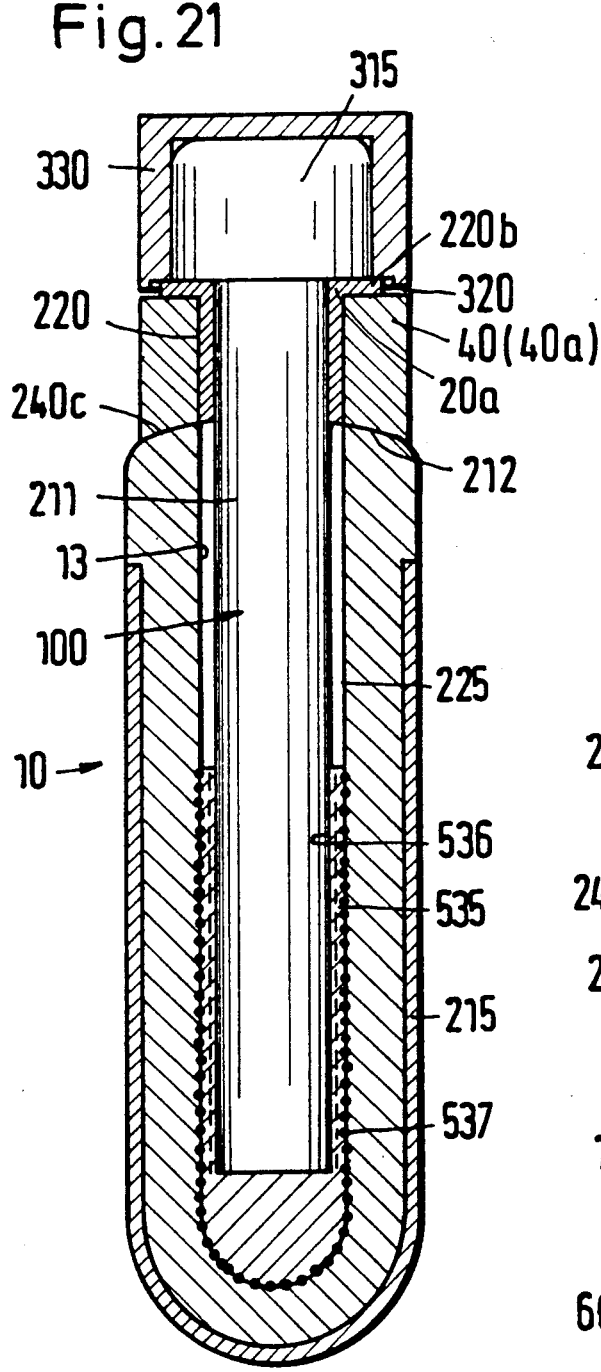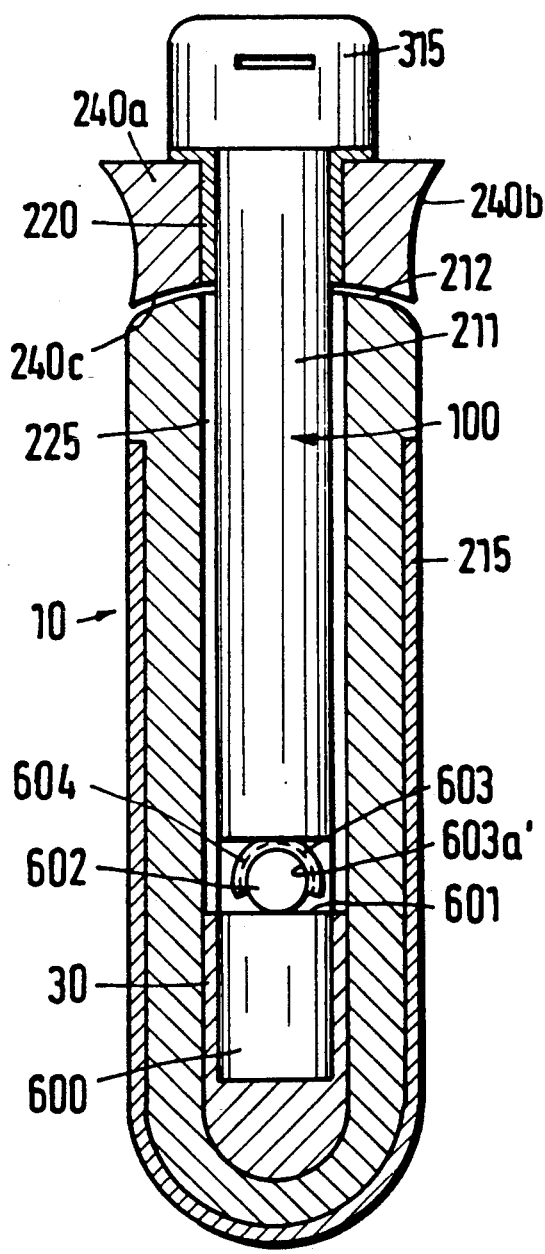

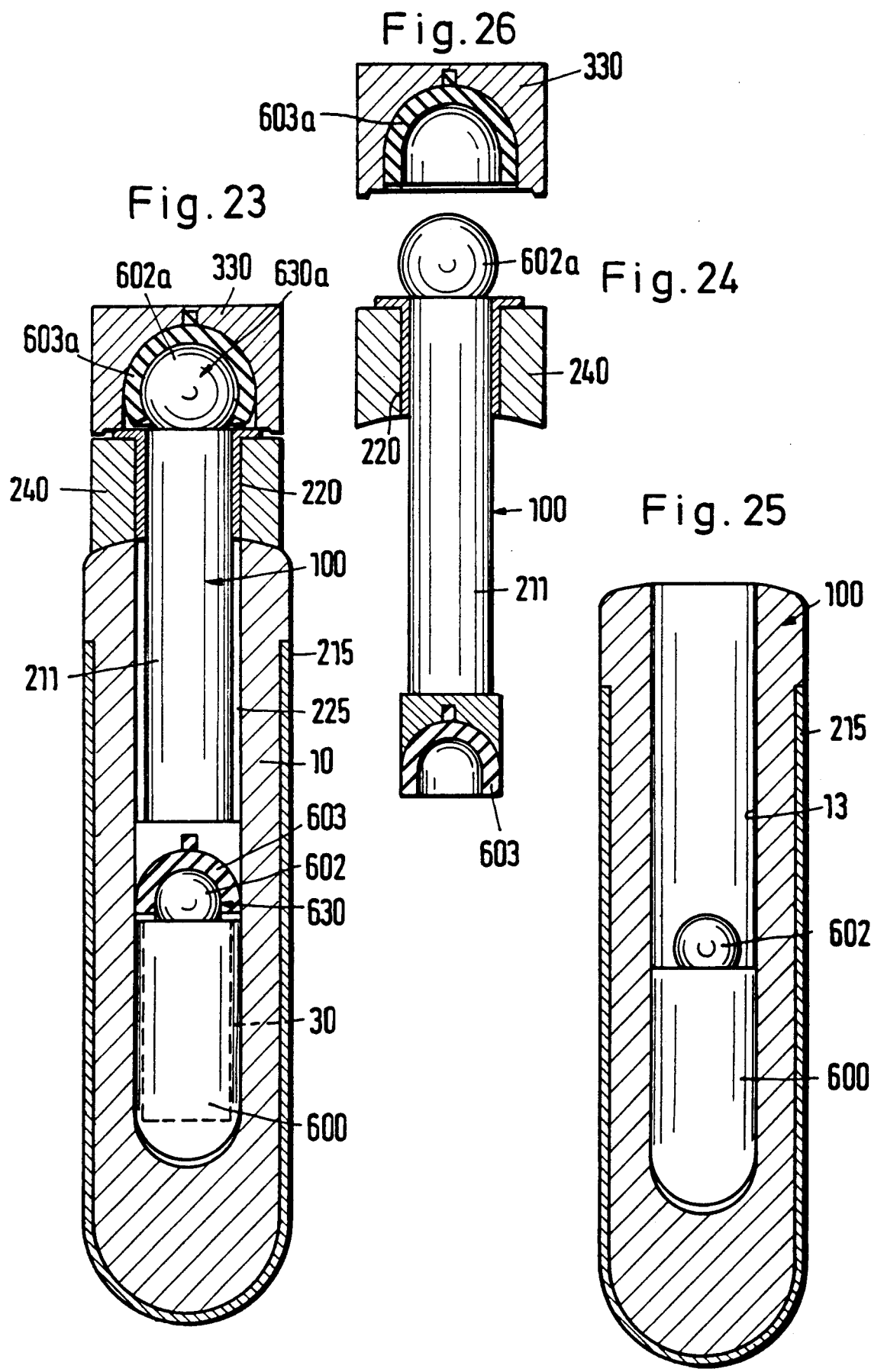

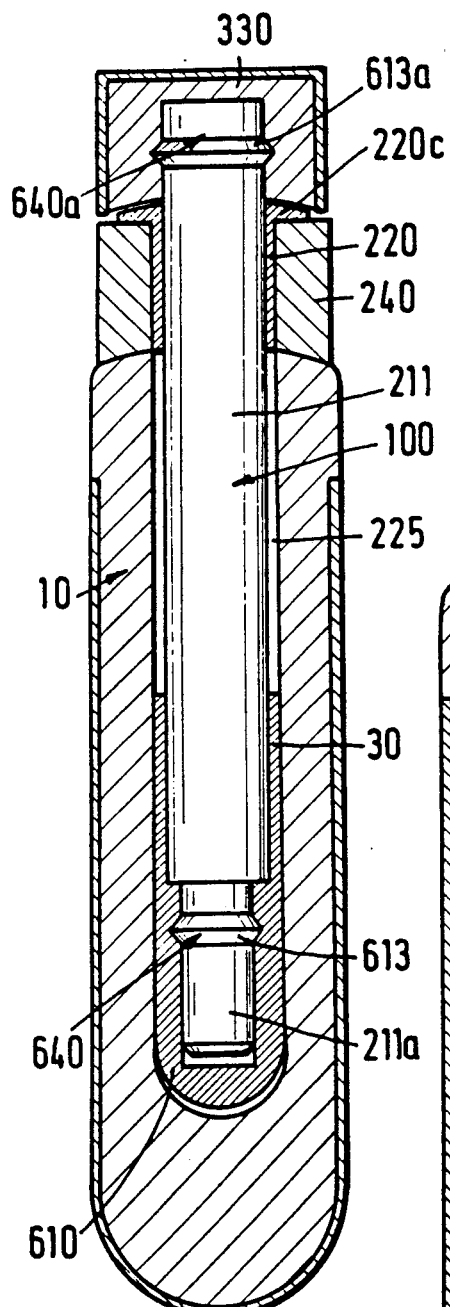
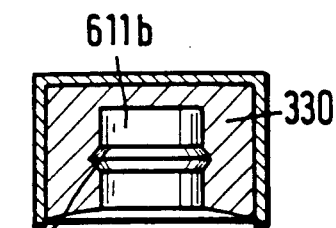
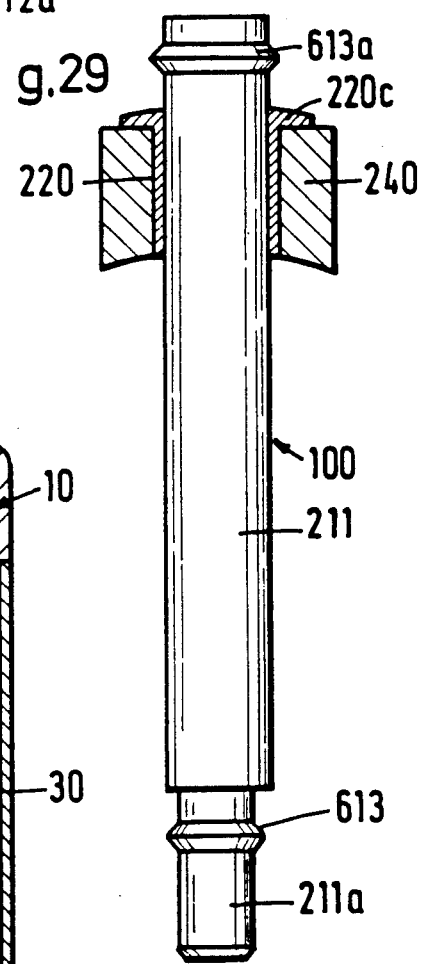
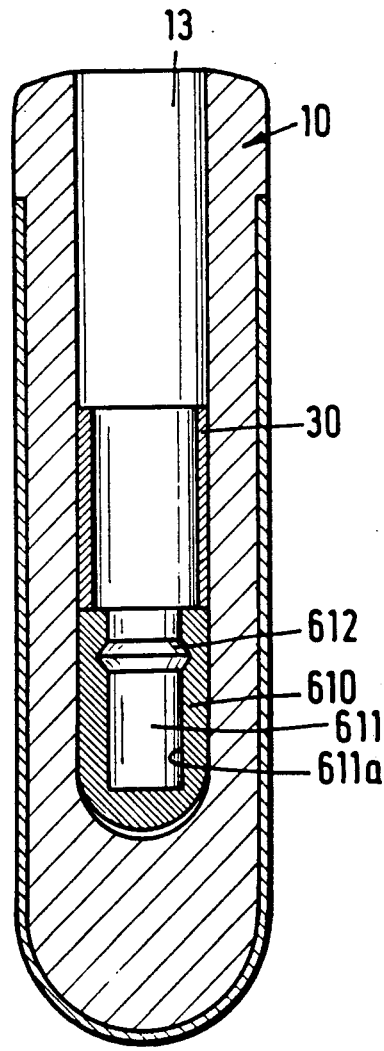

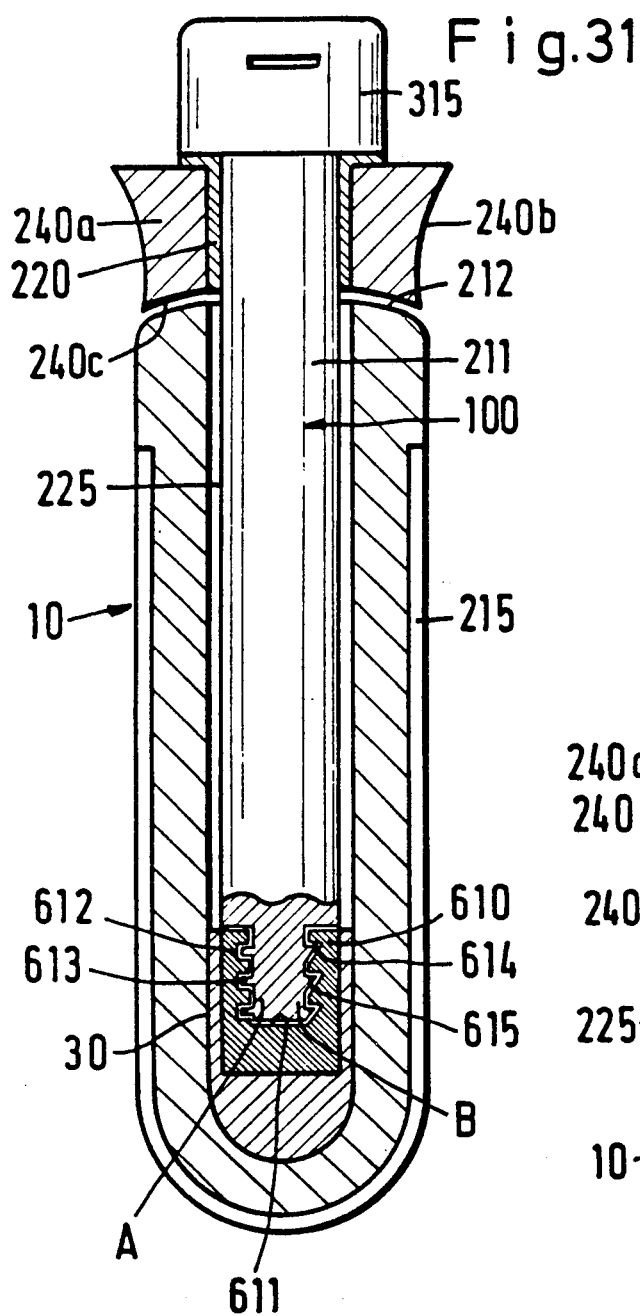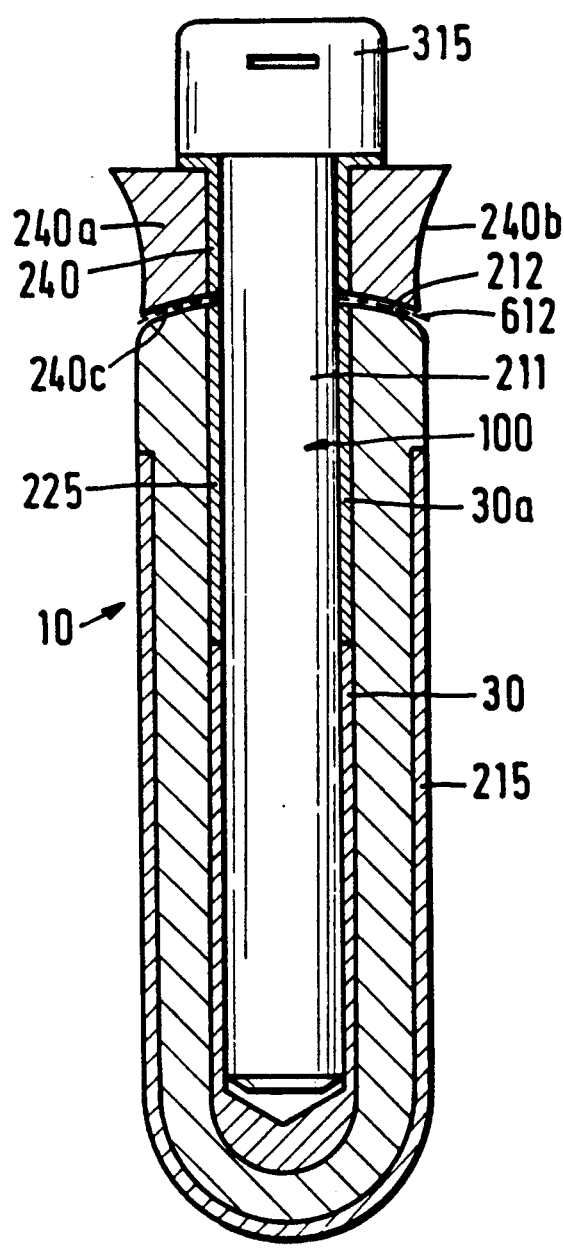

ENOSSAL IMPLANT AND PROCESS FOR INSERTING ENOSSAL IMPLANT INTO THE JAWBONE

This is a continuation of application Ser. No. 07/095,844, filed Sept. 10, 1984, now abandoned, which in turn is a divisional application of Ser. No. 06/795,650 filed 11/6/85, now U.S. Pat. No. 4,731,085 issued Mar. 15, 1988.

BACKGROUND OF THE INVENTION

1. Field of the Invention

The invention relates to an enossal implant for securing a fixed or removable dental prosthesis. The implant includes two interconnectable parts, one part of which is constructed in the form of a primary cylinder with a central longitudinal bore which is placed in the jawbone and is frictionally anchored therein and the other part is constructed as a secondary cylinder which can be placed in the longitudinal bore of the primary cylinder and has a post detachably held therein. The post is constructed at its free upper end for the connection of a dental prosthesis. The invention also relates to a process for inserting an enossal implant in the jawbone.

2. Description of the Related Art

DE-OS 31 49 881 discloses a connecting element for enossal implants. With the aid of the connecting element a loosening of the implant through overloading the implant bearing and the resulting re-formation of the bone is to be prevented. Measures are provided for diverting forces acting on the dental prosthesis perpendicularly to the main axis of the implant into the interior of the latter, so as to bring about a uniform distribution of the stresses exerted by the implant on the implant bed. Therefore, the dental prosthesis is fixed to the spindle made of metal material. The spindle passes coaxially through the inner area of a cup-shaped implant body and is pivotally mounted in a bed of elastic material filling the intermediate area between the spindle and the implant body. The pivot axis is formed by a rotary ball fixed to the spindle. The diameter of the ball corresponds to the inside width of the implant body. However, it is a disadvantage of this implant that the lever fulcrum of the implant post is located roughly in the center of the implant body, so that it is not possible to reliably prevent a loosening of the implant. It is also not possible to reliably ensure the removal of stresses which occur in the outer region of the implant body, so that damage can occur and, in the case of a horizontal compression stress on the dental prosthesis, the implant body can break, particularly if the implant body is made from a ceramic material.

The insertion of such enossal implants which are composed of a primary cylinder and a secondary cylinder into the jawbone takes place in such a way that first a corresponding borehole is prepared in the jawbone and then as the first phase the primary cylinder is inserted in the jawbone bore. This is followed as the second phase by the insertion of the secondary cylinder into the primary cylinder which is frictionally anchored in the jawbone. The prosthesis mount is then screwed onto the connecting attachment of the secondary cylinder and then the prosthesis is joined with the prosthesis mount.

SUMMARY OF THE INVENTION

It is the object of the invention to provide an enossal implant composed of a primary cylinder and a secondary cylinder held in the primary cylinder, wherein the implant is positively and frictionally connected with the bone and in which a load-free stabilization of the primary cylinder is ensured and the implant is not subject to plastic deformation and is maintenance-free. A further object is to ensure a fixed connection of a pin of the secondary cylinder in a longitudinal bore of the primary cylinder, without impairing the oscillating or vibrating property of the pin, wherein the horizontal and/or vertical and/or torsional forces occurring in the mount are conducted into the primary cylinder. In addition, a two-phase implantation process is to be provided using a predetermined and/or given anatomical behavior of the jawbone (provoked atrophy), which ensures the physical effectiveness in the same way as the known two-phase implantation process.

To meet this object according to the invention, an enossal implant is proposed which is constructed in such a way that the implant post of the secondary cylinder is constructed as an oscillating rod or is surrounded by a force line system which diverts the horizontal and/or vertical and/or torsional forces and oscillation securing in the vicinity of the dental prosthesis or in the mount into the lower area of the secondary cylinder and from there into the primary cylinder or into the bottom thereof. The force line system includes an elastic region or several regions with different elastic properties arranged one following the other, such that to a bottom, inelastic region are connected regions with inelasticity and the latter are then followed by regions with strong elasticity, the implant post or oscillating rod being fixed in the primary cylinder by means of a heat seal with an adhesive or being detachably held therein.

The enossal implant may be constructed in such a way that the implant post is of a brittle material and is surrounded by a tubular or annular force line system which diverts the oscillations occurring in the vicinity of the dental prosthesis due to the masseter muscle force acting thereon, while simultaneously displacing the lever fulcrum of the implant post, into the lower region of the secondary cylinder and from there into the primary cylinder. This force line system has a plurality of regions with different elastic characteristics which follow one another, such that a bottom inelastic region is followed by regions with limited elasticity and the latter are then followed by regions with high elasticity. This construction leads to the following advantage. The force line system mounted on the implant post by means of a joining connection, e.g. a frictional connection with anaerobic plastic materials, includes a force line system, e.g. with a modular member or several modular members and, in the latter case, with different elastic properties. Of the superimposed modular members, the bottom modular member has no elasticity and has a rigid construction, like the implant post. The central modular member placed on the bottom modular member is made from a material with a limited elasticity, while the upper modular member is made from a very elastic material, so that under the action of masseter muscle forces, e.g. forces acting horizontally on the dental prosthesis, the fulcrum of the implant post acting as the lever is displaced into the lower region of the primary cylinder or implant body.

The rod-like implant post arranged in the secondary cylinder is made from a brittle material, such as, surgical steel, and forms a lever whose fulcrum is displaced into the lower third of the primary cylinder as a result of the specially constructed force line system. Due to the fact that the implant post is surrounded by modular members, e.g. modular tubes, modular rings, etc, which are made from materials with different elasticities, oscillations occurring at the implant post, e.g. in the case of chewing forces acting at right angles to the implant axis, are intercepted, absorbed by the force line system and diverted into the lower region of the primary cylinder. Thus, the modular members intercept the forces or divert them into the vicinity of the fulcrum, i.e. into the bottom of the implant or primary cylinder, without undergoing deformation or plastic deformation. Since modular members with different elastic properties are used, a force reduction occurs when a force is applied, and the remaining forces are diverted via the implant post of bending-resistant material to the fulcrum in the vicinity of the load or weight arm of the implant post.

Thus, an enossal implant including a primary cylinder and a secondary cylinder held therein and having a force line system is provided, in which the force flux is diverted from the force introduction point in the vicinity of the dental prosthesis via the force line system within the secondary cylinder, then via the force-diverting guide sleeve and via the primary cylinder into the bony implant bearing, so that, apart from a reduction of the load peaks and apart from a reduction of overloading at the implant outlet point from the bone, the fulcrum of the implant post is displaced into the lower region of the implant.

In accordance with an advantageous feature, the secondary cylinder pin is constructed as an oscillating rod. On the pin is arranged an upper modular tube made from a highly elastic material and is joined to the pin by an adhesive. The primary cylinder is provided in the interior of its longitudinal bore with a guide tube located at a distance from the longitudinal bore inlet resulting in a modular tube-free portion forming an air gap when the secondary cylinder is inserted. The guide tube is held in the primary cylinder by means of an adhesive. On the modular tube is arranged an implant attachment with a central through-bore aligned with the longitudinal bore of the primary cylinder. The implant attachment is slidingly held on the primary cylinder surface. The oscillating rod of the secondary cylinder is held in the guide tube by a heat seal arranged on the rod in the vicinity of the guide tube when the secondary cylinder is inserted. An implant constructed in this way provides a frictional and/or positive connection of bone and implant, which is further improved by the external coating of the primary cylinder with a hydroxylapatite ceramic. In addition, the primary cylinder is stabilized in a load-free manner and the secondary cylinder, when ready to assemble, only comprises a single part. There is no need to join together several parts of the secondary cylinder in the mouth of the patient, so that easy, rapid manipulation by a person fitting the implant is ensured. There are no gaps as a result of the construction according to the invention. A constant tensile stress of the secondary cylinder against the primary cylinder is obtained as a result of the heat seal and the sliding zones and because the secondary cylinder is introduced into the primary cylinder under a clearly defined pressure. There is also an imitation of the parodontium because of the sliding action. The implant is absolutely maintenance-free and non-wearing because the implant only had elastically deformable parts which are not subject to plastic deformation, so that there is no longer any need to replace plastically deformable parts. Since the implant is maintenance-free most of the after-care is obviated. This ensures that there are no gaps and considerable time can be saved. The energy flows in the implant can be controlled because plastically deformable parts are avoided. Thus, bioactively coated, body-friendly alumina ceramic can be used which excludes any breakage risk. Due to the fact that the oscillating rod is anchored by the heat seal in the guide sleeve of the primary cylinder following the insertion of the secondary cylinder, vertical, horizontal and torsional forces of a dynamic nature acting on the oscillating rod oscillate the latter and are converted into heat, which is given off into the implant interior. Quantitatively small mechanical energies not converted into heat are supplied to the bone via the primary cylinder in the bearing zone and/or the sealing or securing point, the latter being best position in the center of the vertical axis of the primary cylinder. The oscillation amplitudes are such that the primary cylinder is not mechanically stressed. The angular circumferential edge of the upper modular tube is used for compensating rod compression when vertical forces occur.

The parodontium is imitated by controlled sliding displacement of the implant attachment on the primary cylinder, damped by the permanently elastic upper modular tube. By introducing the secondary cylinder into the primary cylinder under clearly defined pressure, chemisorption ensures that there are no gaps in the vicinity of the sliding zones. The air gap above the guide tube can be filled by a further modular tube made from a permanently elastic material, which then ensures the necessary sealing of the air gap.

According to an advantageous development, the pin of the secondary cylinder is constructed as an oscillating rod and on the pin is arranged an upper modular tube made from a highly elastic material and is connected thereto by an adhesive. The primary cylinder is provided in the inner region of its longitudinal bore with a guide tube which is spaced from the longitudinal bore inlet and provides a section forming an air gap free from a modular tube when the secondary cylinder is inserted. The guide tube is held in the primary cylinder by means of an adhesive. On the modular tube is placed an implant attachment with a central opening aligned with the longitudinal bore of the primary cylinder. The implant attachment is slidingly held on the surface of the primary cylinder. The lower region of the secondary cylinder oscillating rod is fixed to the guide tube by an adhesive. An implant constructed in this way provides a positive and/or frictional connection between bone and implant. The connection is further improved by the external coating of the primary cylinder with a hydroxyl-apatite ceramic. In addition, the primary cylinder is stabilized in a load-free manner and, when ready to assemble, the secondary cylinder only comprises a single part. There is no need to join together several individual parts of the secondary cylinder in the mouth of the patient, so that easy, rapid manipulation is ensured. There are no gaps as a result of the construction according to the invention. A constant tensile stress of the secondary cylinder against the primary cylinder is obtained by the heat seal and the sliding zones and because the secondary cylinder is introduced into the primary cylinder under a clearly defined pressure. The parodontium is imitated by the sliding action. The implant is completely maintenance-free and non-wearing because the implant only has elastically deformable parts which are not subject to any plastic deformation, so that there is no longer any need to replace plastically deformable parts. Since the implant is maintenance-free, most of the after-care is obviated. This ensures that there are no gaps and considerable time can be saved. The energy flows in the implant are controllable because plastically deformable parts are avoided, so that the use of bioactively coated, bodyfriendly alumina ceramic is furthered and a breakage risk is excluded. Due to the fact that the oscillating rod is fixed to the primary cylinder guide sleeve after inserting the secondary cylinder, vertical, horizontal and torsional forces applied dynamically to the oscillating rod cause the latter to oscillate and the oscillations are converted into heat, which is given off to the interior of the implant. Quantitatively small mechanical energies not converted into heat are transferred via the primary cylinder to the bone in the bearing region or securing point, which is best located in the center of the vertical axis of the primary cylinder. The oscillation amplitudes are such that the primary cylinder is not mechanically stressed. In addition, the fixed connection of the oscillating rod to the guide sleeve which, in turn, is fixed to the primary cylinder, ensures that oscillations can be better monitored and controlled.

The imitation of the parodontium is effected by a controlled sliding displacement of the implant attachment on the primary cylinder, damped by the permanently elastic upper modular tube. Through the introduction of the secondary cylinder into the primary cylinder under a clearly defined pressure, gaps are prevented in the vicinity of the sliding zones.

It has been found that ceramic upper parts, such as, a mucous membrane sleeve, can break under limited forces of e.g. 5 Kp. This is due to the fact that the spherical surface of the primary cylinder is forced in a wedge-like manner into the ceramic upper part when higher forces are applied, so that the ceramic upper part can be broken as a result of the wedge action.

However, it is not possible to eliminate the spherical surfaces because the "rotary effect" of the implant ensures its universal usability. In addition, the central oscillating rod has the oscillation behavior of a freely oscillating rod. The oscillating rod still freely oscillates in the implant in the case of horizontal forces which represent 250% of those conventionally encountered in the mouth, i.e. the oscillating rod can fully develop its damping action. It has been found that the sealing of the ceramic upper part against the ceramic lower part and the sliding characteristics (friction) cannot be modified by increased pressing of the upper part against the lower part and in fact only limited pressing is required to ensure the necessary sealing and sliding.

It was therefore necessary that the vertical forces acting on the implant attachment or the oscillating head of the implant are absorbed in the implant base and not on the ceramic upper part.

In accordance with another development, the guide tube is omitted. The oscillating rod is connected by means of a screw connection or some other suitable, equivalent connection, to a shaped member having an upper borehole for receiving the rod. The shaped member is held in the interior of the primary cylinder by means of an adhesive and fills the entire space previously used by the guide tube including the cavity below it between the bottom end of the previously provided guide tube and the primary cylinder bottom. As a result of this configuration, the forces applied perpendicularly to the oscillating head of the implant are directly displaced to and act on the implant bottom. The bottom of the primary cylinder is made from a ceramic material. Thus, pressure is relieved from the ceramic upper part. Only forces resulting from compression of the oscillating rod when force is applied to the oscillating or assembly head can have an effect.

However, there is only a slight reduction to the length of the oscillating rod, e.g. $41\mu$ when a force of 80 Kp is applied. Such a compression is absorbed by the elasticity of the upper plastic modular tube, so that a pressure can no longer be exerted on the upper ceramic part, i.e. the mucous membrane sleeve, in such a way that it breaks. This construction also makes it possible to position two ceramic parts of the implant in the form of spherical surfaces adjacent to one another, without unduly stressing and breaking the ceramic upper parts.

The invention also relates to a process for inserting the enossal implant in the jawbone for securing a fixed or removable dental prosthesis, in which the enossal implant includes two interconnectable parts wherein one part is constructed as a primary cylinder with a central longitudinal bore to be introduced into the jawbone and anchored therein in a frictional manner, while the other part is constructed as a secondary cylinder having a pin which can be introduced into the longitudinal bore of the primary cylinder and is held therein and which at its free upper end is constructed for the connection of the dental prosthesis. The process includes providing a depression in the jawbone, wherein the depression has a larger diameter than the implant to be inserted and a depth which is less than the implant length. An actual borehole for receiving the implant is cut centrally with respect to the depression. The actual bore has a diameter roughly corresponding to the external diameter of the implant. During a first phase, the implant comprising a first cylinder and a second cylinder assembled outside the jawbone is inserted in the borehole, so that the connecting attachment for the prosthesis comes to rest in the depression and the mucous membrane forms a top closure or seal. This is followed by a provoked bone atrophy and the release of the connecting attachment of the implant during the bone atrophy. In a second phase, the prosthesis mount is fixed and then the prosthesis is connected thereto.

The invention also relates to a process for inserting an enossal implant in the jawbone for fixing a fixed or removable dental prosthesis, in which the enossal implant includes two interconnectable parts, wherein one part is constructed as a primary cylinder with a central longitudinal bore to be introduced into the jawbone and anchored in a frictional manner therein and the other part is constructed as a secondary cylinder having a pin which can be introduced into the longitudinal bore of the primary cylinder and is held therein, and its free upper end is constructed for the connection of the dental prosthesis. The secondary cylinder pin is constructed as an oscillating rod and on the pin is arranged an upper modular tube of a highly elastic material which is connected to the pin by adhesive connection. In the interior of the longitudinal bore, the primary cylinder has a guide tube located at a distance from the longitudinal bore inlet resulting in a portion which is module tube-free and forms an air gap when the secondary cylinder is inserted. The guide tube is held in the primary cylinder by means of an adhesive. On the modular tube is arranged an implant attachment with a central through-bore aligned with the longitudinal bore of the primary cylinder. The implant attachment is slidingly held on the surface of the primary cylinder. The lower region of the secondary cylinder oscillating rod is fixed to the guide tube by means of an adhesive. The process includes making a depression in the jawbone, wherein the depression has a larger diameter than the implant to be inserted and a depth which is less than the implant length. The actual borehole for receiving the implant is cut centrally with respect to the milled depression. The actual borehole has a diameter roughly corresponding to the external diameter of the implant. In a first phase, the implant comprising primary cylinder and secondary cylinder and assembled outside the jawbone is inserted in the borehole, so that the connecting attachment for the prosthesis comes to rest in the depression and the mucous membrane forms a top closure. This is followed by a provoked bone atrophy and the release of the joining attachment of the implant. In a second phase, the prosthesis mount is screwed down and afterwards the prosthesis is connected thereto.

Although the finished implant composed of primary cylinder and secondary cylinder is inserted in the prepared borehole in the jawbone, this process for inserting an enossal implant in the jawbone for securing fixed or removable dental prosthesis according to the invention constitutes a two-phase implantation process making use of a provoked bone atrophy. Although it is a two-phase implantation process, the entire actual implant is in fact implanted in the first phase. This is made possible by the predeterminable anatomical behavior of the jawbone, i.e., a provoked bone atrophy. This is because, while in the known implantation process initially the primary cylinder is implanted and then secondary cylinder is inserted in the primary cylinder, in the process according to the invention, the complete implant comprising primary cylinder and secondary cylinder is implanted in a first phase, so that the healing of the implant in the jawbone can take place without stressing prior to the start of atrophy. As a result of the atrophy, the head, i.e. the connecting attachment, is released and simultaneously the mucous membrane is adapted to the atrophy and the resulting jawbone configuration. The second phase then comprises mounting the prosthesis mount on the implanted implant.

The various features of novelty which characterize the invention are pointed out with particularity in the claims annexed to and forming a part of this disclosure. For a better understanding of the invention, its operating advantages attained by its use, reference should be had to the drawing and descriptive matter in which there are illustrated and described preferred embodiments of the invention.

BRIEF DESCRIPTION OF THE DRAWING

In the drawing:

FIG. 3 is a vertical sectional view of the secondary cylinder according to FIG. 1;

FIG. 4 is partly an elevational and partly a vertical sectional view of another embodiment of an enossal implant with a heat seal comprising a primary cylinder and a secondary cylinder with a pin constructed as an oscillating rod;

FIG. 9 is a vertical sectional view of the secondary cylinder of the implant according to FIG. 7;

FIG. 10 is partly an elevational and partly a vertical sectional view of another embodiment of an enossal implant with a differently constructed heat seal;

FIG. 11 is a view of a detail of the transition region between the modular tube, implant attachment and secondary cylinder in the embodiment of FIG. 10;

FIG. 14 is a vertical sectional view of the secondary cylinder according to FIG. 12;

FIG. 15 is partly an elevational and partly a vertical sectional view of another embodiment of an enossal implant with an oscillating rod bonded into the guide tube and with spherical sliding surfaces;

FIG. 16 is a vertical sectional view of the primary cylinder of the implant according to FIG. 15;

FIG. 17 is a vertical sectional view of the secondary cylinder of the implant according to FIG. 15;

FIG. 21 is partly an elevational and partly a vertical sectional view of another embodiment of an enossal implant with an oscillating rod held in the primary cylinder by means of a base part;

FIG. 22 is partly an elevational and partly a vertical sectional view of another embodiment of an enossal implant in which the oscillating rod is held in the primary cylinder by means of a detachable clamp fastener;

FIG. 23 is partly an elevational and partly a vertical sectional view of another embodiment of an enossal implant in which the oscillating rod of the secondary cylinder is held in the primary cylinder and the assembly head is held on the oscillating rod by means of detachable clamp fasteners;

FIG. 24 is partly an elevational and partly a vertical sectional view of the secondary cylinder of the enossal implant of FIG. 23;

FIG. 25 is partly an elevational and partly a vertical sectional view of the primary cylinder of the enossal implant of FIG. 23;

FIG. 26 is a vertical sectional view of an assembly cap which can be placed on the oscillating rod of the secondary cylinder;

FIG. 27 is partly an elevational and partly a vertical sectional view of another embodiment of an enossal implant in which the oscillating rod of the secondary cylinder is held in the primary cylinder and the assembly head is held on the oscillating rod by means of an undetachable clamp fastener;

FIG. 28 is partly a elevational and partly a vertical sectional view of a primary cylinder of an enossal implant according to FIG. 27;

FIG. 29 is partly a elevational and partly a vertical sectional view of the secondary cylinder of an enossal implant according to FIG. 27;

FIG. 30 is a vertical sectional view of the assembly cap which can be placed on the secondary cylinder oscillating rod;

FIG. 31 is partly an elevational and partly a vertical sectional view of an enossal implant in which the oscillating rod is held in the primary cylinder by means of an undetachable spring catch; and FIG. 32 is partly an elevational and partly a vertical sectional view of an enossal implant with a device for sealing gaps in the vicinity of the spherical surfaces between the primary cylinder and the implant attachment.

DESCRIPTION OF THE PREFERRED EMBODIMENT

Figure 1:
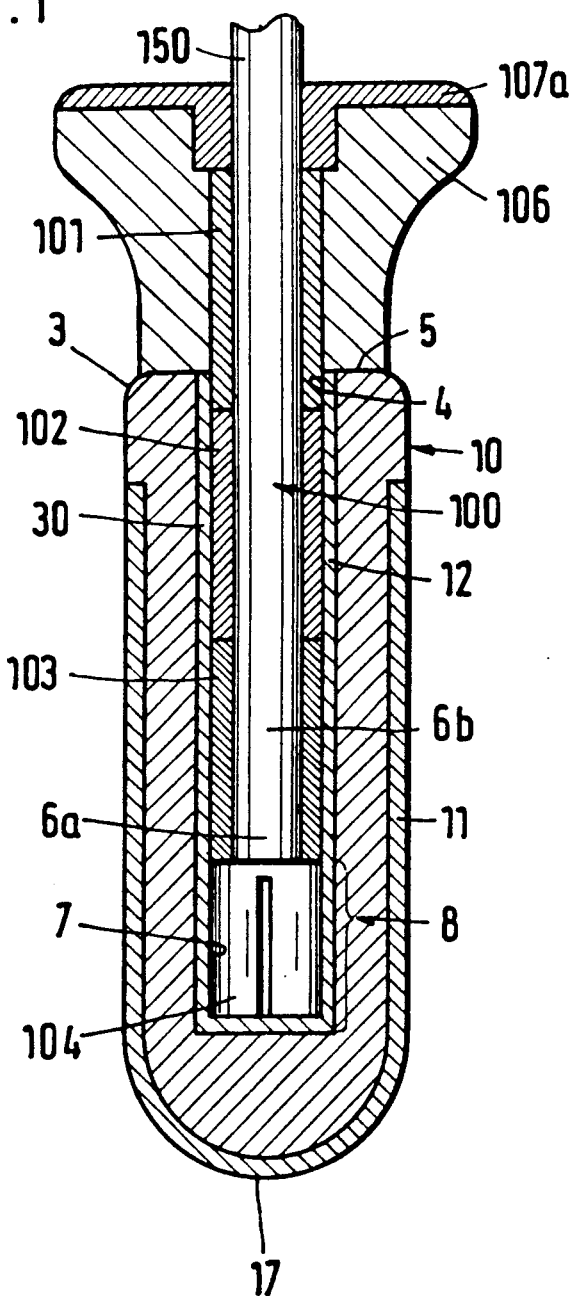
FIG. 1 is an elevational and partly a vertical sectional view of an enossal implant comprising a primary cylinder and a secondary cylinder with a force line system comprising three modular tubes.

The enossal implant shown in FIG. 1 includes a primary cylinder 10, which is the so-called reception cylinder, and a secondary cylinder 100, which is the so-called working cylinder.

Figure 2:
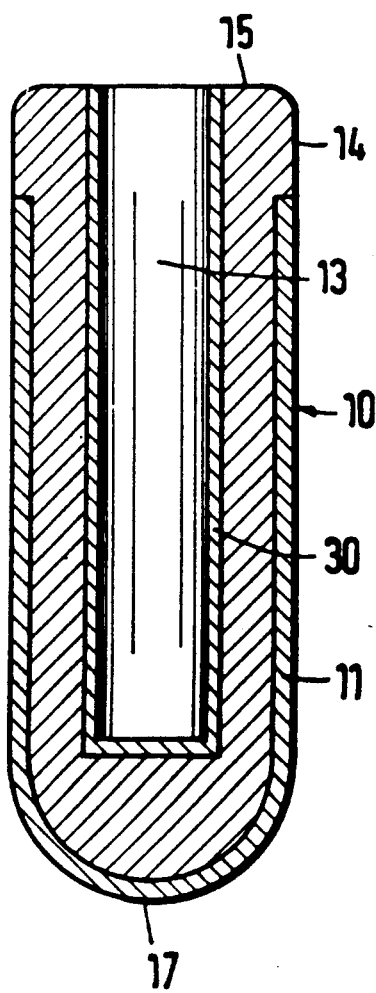
FIG. 2 is a vertical sectional view of the primary cylinder according to FIG. 1.

The enossal implant primary cylinder 10 includes a bending-resistant body which is made of alumina ceramic. The primary cylinder 10 is externally coated with a hydroxylapatite ceramic which is designated 11 in FIG. 2. The primary cylinder 10 is the actual implant body or material carrier and has a central longitudinal bore 13 forming an inner area (FIG. 2).

The secondary cylinder 100 is inserted in the longitudinal bore 13 of primary cylinder 10, for example, approximately 3 months after the implantation of the primary cylinder 10, so that the connection between the implant and the dental prosthesis is formed.

In the inner area or in the longitudinal bore 13 of primary cylinder 10 is placed a guide tube 30 which roughly extends over the entire length of longitudinal bore 13 and permits the effortless insertion of the secondary cylinder 100 into the primary cylinder 10. This guide tube 30 is also part of a force line system of the enossal implant which, like modular members 101, 102, 103, 104 of the force line system described below, may be of different materials. As a result of the elastic deformation of guide tube 30 in primary cylinder 10, it is possible to achieve an additional force reduction. The remaining forces are diverted into crystallographically specific directions, e.g., into the lower regions of the primary cylinder 10. When using and producing guide tube 30, so-called monocrystals are of considerable technical significance. Thus, oscillatable or vibratable metal provides an elastically deformable envelope for the secondary cylinder 100 mounted in the primary cylinder 10. In particular, it is possible to grow and use monocrystalline materials with predetermined defects, so that the elastic deformation of guide tube 30 is controllable, e.g., in conjunction with the force transfer from secondary cylinder 100 to primary cylinder 10.

According to FIG. 3, secondary cylinder 100 has a pin 105 which ca be introduced into bore 13 of primary cylinder 10, so that secondary cylinder 100 becomes exchangeable. The diameter of the cylindrical outer wall 112 or of a part of the outer wall of pin 105 of secondary cylinder 100 is larger than the diameter of longitudinal bore 13 of primary cylinder 10, so that pin 105 or a part thereof, e.g. part 104, is clampingly held at body temperature in the longitudinal bore 13, but in the case of a temperature reduction can be detached or removed from the longitudinal bore of the primary cylinder. Such a connection is relatively simple. The connection cannot be loosened and is substantially free of gaps, so that no bacteria form and the inflammation cannot occur.

The secondary cylinder 100 is formed by an implant post 150 whose upper free end carries a detachable sealing or locking device for the dental prosthesis, not shown in the drawing. Moreover, the secondary cylinder 160 includes an implant attachment 106 which is made of known materials, such as, alumina ceramic. The top of the implant attachment 106 can be covered by a cover plate 107a which is provided with an inwardly directed, neck-like extension 107b which surrounds the upper area of the implant post 150 (FIG. 3).

Secondary cylinder 100 also houses the so-called force line system which is formed by the modular members 101 to 104. This system is particularly suitable for rotationally symmetrical cylindrical implants according to FIG. 1, preferably made of alumina ceramic, but can also be used for implants of other types or designs. This force line system with implant post 150 is a force-transferring, material binding element, which diverts the flux of force from the force introduction point into the bony implant bearing 2, such that the load peaks are reduced and no overloading of the outlet point 3 of the enossal implant from the bone occurs (FIG. 1).

This force-transferring, material binding element of secondary cylinder 100 (FIG. 3) is composed of modular members 101 to 104, which may be tubular or annular members and are mounted on implant post 150. This force-transferring, material binding element may also include guide tube 30, in addition to the modular members 101 to 104. After introducing the secondary cylinder 100 into the longitudinal bore 13 of primary cylinder 10, the secondary cylinder 100 is surrounded and secured by guide tube 30 which is located in the longitudinal bore 13 of primary cylinder 10.

The force line system is composed of modular members 101 to 104 which are arranged next to each other. The modular members have roughly the same length, but have different elastic characteristics (FIGS. 1 and 3). The modular elements may also have different lengths.

The lower modular member 103 with or without part 104 is made from an inelastic material and is constructed in the same rigid manner as implant post 150. On lower modular member 103 is placed a further, central modular member 102 which is made of a material with a limited elasticity. The third modular member 101 is made of a very elastic material. The modular member may also be made from a polycrystalline or monocrystalline material, a rigid plastic material or some other suitable plastic material with corresponding elastic characteristics. The other modular members are made from corresponding materials so as to be adapted to the particular elasticity required, wherein it is also possible to use plastic materials, e.g. silicone rubber, with differing degrees of hardness and elasticity. It is also possible to use other suitable materials and further reference will be made thereto hereinafter.

It is also possible to construct the modular members 101 to 104 in one piece, wherein the resulting force line system has three or more regions with different elastic characteristics. The lower region is constructed inelastically, the central region has a limited elasticity and the upper region of the force line system has a high elasticity. The force line system extends with its upper modular member into implant attachment 106 (FIG. 3).

The guide tube 30 may extend into the region of implant attachment 106, so that the guide tube is also located in the implant attachment. During the assembly of secondary cylinder 100, the guide tube 30 is fixed to attachment 106. At the bottom, guide tube 30 is longer than the implant attachment 106, so that the guide tube projects by approximately 1 to 3 mm from the longitudinal bore 13 of primary cylinder 10 below the bearing surface of the implant attachment.

However, the guide tube 30 need not extend into the implant attachment 106. In this case, the upper modular member 101 is a guide member which engages in longitudinal bore 13 of primary cylinder 10 and is in metallic contact with guide tube 30 in primary cylinder 10, as indicated at 4 in FIG. 1. The guide tube places the bearing surfaces of primary and secondary cylinders into absolute contact, particularly since these bearing surfaces 15, 108 of the primary cylinder 10 and secondary cylinder 100 are polished, so that there is a tight seal 5 between primary cylinder 10 and implant attachment 106 or secondary cylinder 100 (FIGS. 1 and 3).

The force line system obtained by using modular members results in the diversion of a masseter muscle force acting on implant post 150, which is indicated by arrows 1 in FIG. 1 and which may include a horizontally acting force. However, the implant post 150 of the enossal implant should be connected to neighboring teeth or implants by a suitable dental prosthesis, so that the support on the neighboring implant or tooth makes it possible to compensate the cause of a rotary movement or the so-called torque which is a product of the force times lever or moment arm with respect to the rotation axis. During this phase of integration of the post, the force acting on the implant, i.e., the horizontal force, is equally distributed over all the interconnected posts and the portion remaining for the force line system or enossal implant acts in the region of the lower modular member 103, 104 which is of an inelastic material, e.g., a polycrystalline material. Specifically, the remaining portion acts in the lower third of the primary cylinder 10. This lower modular member 103, 104, like implant post 150, is made of a brittle material with a high modulus of elasticity. This leads to a uniformly distributed, greatly reduced stress in the bony implant mount or bearing 2 (FIG. 1).

The elastic deformation properties of modular members 101 to 104 which act as so-called vibration dampers, and the resulting uniform movement of the implant post 150 about its rest position, lead to a force diversion which results in a reduction of the stress peaks, particularly if the lower modular member 103, 104 has a much higher modulus of elasticity than the upper modular member or is made of very brittle material, so that a major part of the force is diverted into a spherical base 17 of the enossal implant (FIGS. 1 and 2). A feature of the force line system is the implant post 150 which is surrounded by the different modular members 101 to 104. This post 150 does not undergo a shape and configuration change under force and acts in a mainly oscillating manner after assembly of the complete system, while the modular members undergo elastic deformation.

The implant post 150 may be of a polycrystalline material, e.g., a metal with a high modulus of elasticity. It has been found that the plastic characteristics of a metal material with monocrystalline or polycrystalline structure is determined by factors which lead to deviations of the real lattice from the ideal lattice. More particularly, the deviations relate to different types of lattice defects which partly result from the crystal growth, but partly are formed by external effects, e.g. the manufacture and processing of the metal. Each lattice defect is a component for the plastic behavior of a material under the effect of forces which are well below the theoretical shear strength of a so-called monocrystal. Most metals or crystals have plasticity. If external forces act on these metal bodies, e.g. on the implant post 150, then there is a permanent change of their shape before they start to break, unlike in the case of brittle materials, e.g. implant post 150, in which a break occurs when specific stress limits are exceeded.

Thus, if in the case of a plastically deformed body the force acting thereon is removed, the deformations only partly return to the original shape and mostly they remain as so-called shape changes. On the other hand, in the case of elastically deformed members, e.g. implant post 150, the deformations are removed again on removing the force. Therefore, implant post 150 is made of a brittle material. The thickness of the implant post 150 is based on a specific stress limit, wherein the masseter muscle force is assumed as the external force. As a result of the cross-section and length of implant post 150, it is prevented that a specific stress limit is exceeded and, consequently, the breaking of the implant post is prevented. Under these conditions, the post oscillates as a body with uniform movement about its position of rest.

If a polycrystalline body, e.g. the implant post 150, is plastically extended by a tensile deformation, it is uniformly constricted on all sides. However, a monocrystal, e.g. one of tubular modular members 101 to 103 or an annular modular member, assumes an elliptical cross-section. In the case of a monocrystal, e.g. the thin, oscillating metal sheet of modular members 101 to 104 and guide tube 30, crystallographically defined planes of the lattice or so-called sliding planes slide on one another in crystallographically defined directions o sliding directions. This sliding process is of significance, for example, in the case of a masseter muscle force 1 acting on the implant post 150, on modular members 101 to 104, as well as on guide tube 30 in primary cylinder 10. It has been found that the monocrystals have a major technical significance as an elastically deformable envelope of implant post 150, i.e. the complete force line system formed from modular members 101 to 104. The force line system is in part formed by an elastically deformable intermediate layer between implant post 150 and primary cylinder 10. Through the use of suitable metal materials, e.g. monocrystals with predetermined defects and so-called impurities, the elastic deformations of the modular members and of guide tube 30 can be controlled in conjunction with the characteristic mobility of the teeth or the intramobility of further implants.

Whether and to what extent a crystal, or a material from which the modular members and guide tube or tubes are formed, is deformable is dependent on factors, such as the structure, temperature, deformation type, etc., wherein it is possible to use a multipart guide tube instead of a one-part tube.

If in the force line system a modular member is exposed to a force, for example, resulting from oscillations of implant post 150, then the modular member undergoes shape changes, i.e., the thin, oscillatable metal from which the modular member is made is elastically deformed. If during the deformation the forces acting on the modular members do not exceed a specific value, this deformation is elastic or reversible. However, if the elastic limit is exceeded, either a plastic deformation occurs or the material of the modular member or of the guide tube or primary cylinder of the enossal implant is broken. Thus, the elastic shape changes or deformations of modular members 101 to 104 are dependent on the structure of the material. Apart from monocrystalline materials, it is also possible to use polycrystalline materials for producing the modular members.

The secondary cylinder 100 is fixed in the inner area or in the longitudinal bore 13 of primary cylinder 10 by means of a known device, for example, a heat seal or thermal closure indicated at 104 in FIG. 3. The secondary cylinder 100 may be fixed by jointing connections 110, such as, an integral joint with anaerobic plastic materials or other suitable materials.

Implant post 150 and the lower modular member 104 are made of a brittle material with a high modulus of elasticity and both are made from materials with the same modulus of elasticity. If a force 1 acts in the upper region of the dental prosthesis, the implant post 150 acts as a lever. The lever fulcrum is located approximately in the lower third of primary cylinder 10, if the lower modular member and the implant post 150 are made of brittle material with a high modulus of elasticity and the modular members 101, 102, 103 above the lower modular member are made of elastically deformable materials. The lever fulcrum located in the lower third of primary cylinder 10 is indicated at 6a in FIG. 1.

Due to the fact that implant post 150 is fixed to the lower modular members 104 and 110 (FIG. 3), for example by means of jointing connections or the like, and are in turn clamped into guide tube 30 in primary cylinder 10, as indicated at 7 in FIG. 1, a further auxiliary fulcrum 6b is formed when a horizontal force acts on the upper region of the dental prosthesis. If the implant post 150 is disturbed by a force acting on the dental prosthesis, the implant post 150 transfers the oscillations to the lower modular member which starts to oscillate because of its fixed fitting in guide tube 30 of primary cylinder 10 and because it has the same modulus of elasticity as implant post 150. As a result, a plurality of oscillation fields are formed, namely, one around the actual lever fulcrum 6a, one around the auxiliary fulcrum 6b and another in the entire area of the lower modular member. As a result, the force is vertically displaced downwardly and beyond the lower modular member 104 not at a point but over the entire length of the lower modular member to primary cylinder 10 and from there to the bone.

The center of the lower modular member 103 is located in the so-called rotation center 6b of the implant which, in turn, is located in the center of primary cylinder 10. Thus, the implant post 150 and the lower modular members 103, 104 cause a vertical force displacement and simultaneously a force distribution, such that a force occurring at the force application point 1 or on the dental prosthesis only acts with part of the original force in the force dispensing region (FIG. 1).

Figure 5:
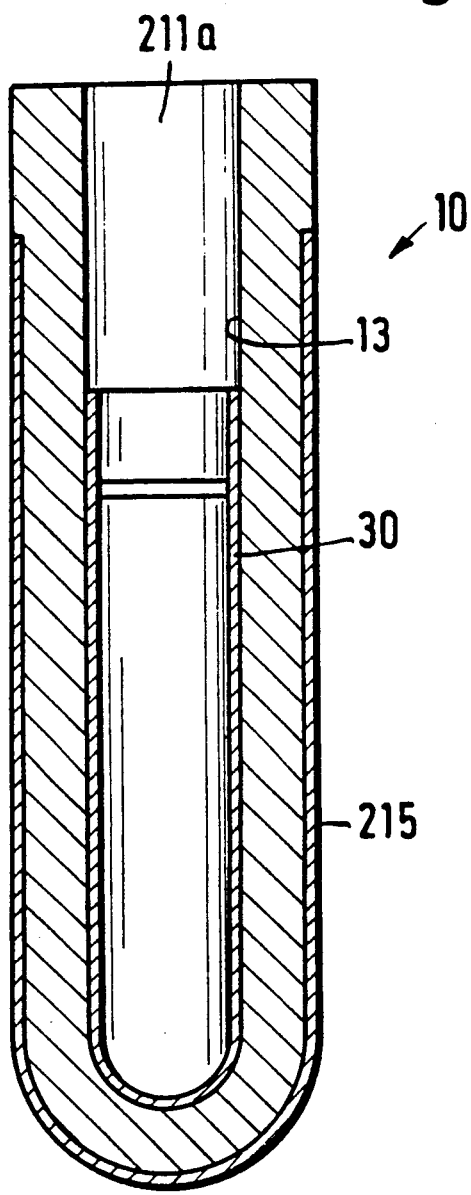
FIG. 5 is a vertical sectional view of the primary cylinder according to FIG. 4.
Figure 6:
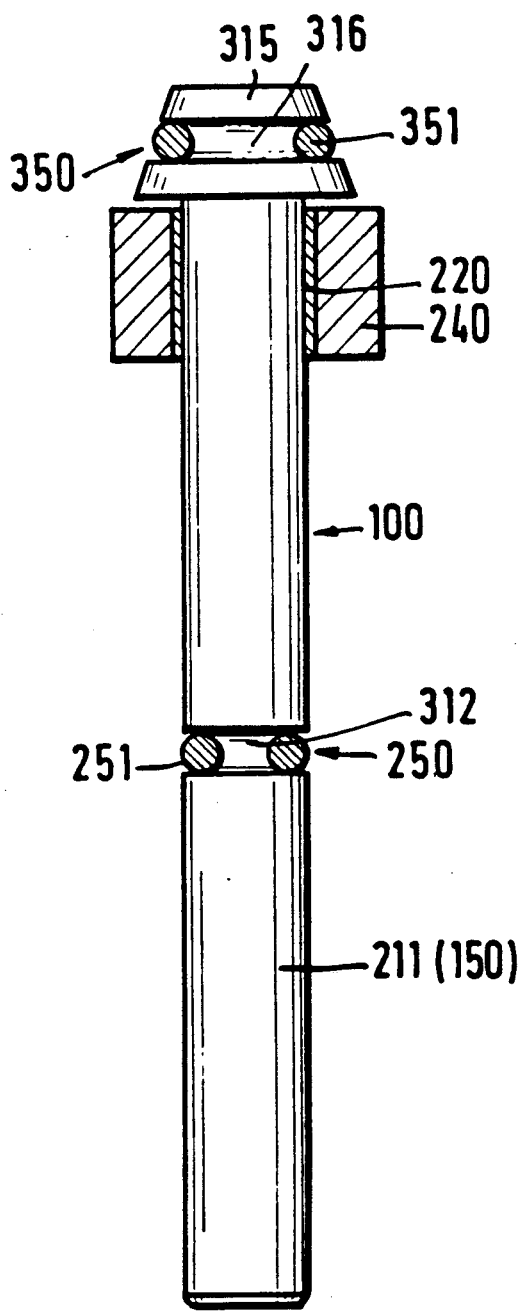
FIG. 6 is a vertical sectional view of the secondary cylinder according to FIG. 4.

The enossal implant shown in FIGS. 4 to 6 also includes a primary cylinder 10 and a secondary cylinder 100.

Primary cylinder 10 includes a bending-resistant body, particularly of alumina ceramic and is externally coated with hydroxyl-apatite ceramic. This external coating is designated 215. As can be gathered from FIG. 5, the external coating 215 does not extend over the entire area of the primary cylinder 10, as will be discussed further hereinafter.

Primary cylinder 10 is the actual implant body and has a central longitudinal bore 13, which forms the inner area.

Following the implantation of the primary cylinder 10, i.e. approximately 3 months after the implantation, the secondary cylinder 100 is inserted in longitudinal bore 13 of the primary cylinder 10, so that the connection between implant and dental prosthesis is formed.

The secondary cylinder 100 has a pin constructed as an oscillating rod 211 or an implant post 150. An upper modular tube 220 made of a highly elastic material is mounted on implant post 150. The tube 220 can also be of a metal, plastic material or other suitable material. This modular tube 220 is positioned in the upper region of the oscillating rod 211 of secondary cylinder 100 and is held thereon by means of an adhesive connection.

A guide tube 30 is provided in the inner area of a longitudinal bore 13 of primary cylinder 10 and spaced from opening 211a of bore 13. A modular tube is not provided in the section between modular tube 220 and guide tube 30. Rather, an air gap 225 (FIG. 4) is formed when secondary cylinder 100 is inserted in primary cylinder 10. Guide tube 30 which extends over a larger part of the length of primary cylinder 10 is fixed in the latter by means of an adhesive.

The secondary cylinder 100 is composed of a pin which is insertable in the longitudinal bore 13 of primary cylinder 10. The pin is formed by an oscillating rod 211 made of suitable materials. The secondary cylinder 100 also includes an upper head-like extension 315, or oscillating head, which forms the fitting head and which receives a fitting cap 330 which is detachably held on the oscillating head 315.

The implant attachment 240 is mounted on modular tube 220 and is provided with a central through-bore 241 whose diameter corresponds to the external diameter of tube 220. In the embodiment of FIGS. 4 and 6, implant attachment 240 has a cylindrical shape and an external diameter roughly corresponding to the external diameter of primary cylinder 10. However, the external diameter of implant attachment 240 can also be smaller than that of the primary cylinder 10, so that the external diameter of implant attachment 240 coincides with that of the fitting cap 330. The latter is made from metal materials, particularly precious metals.

Figure 7:
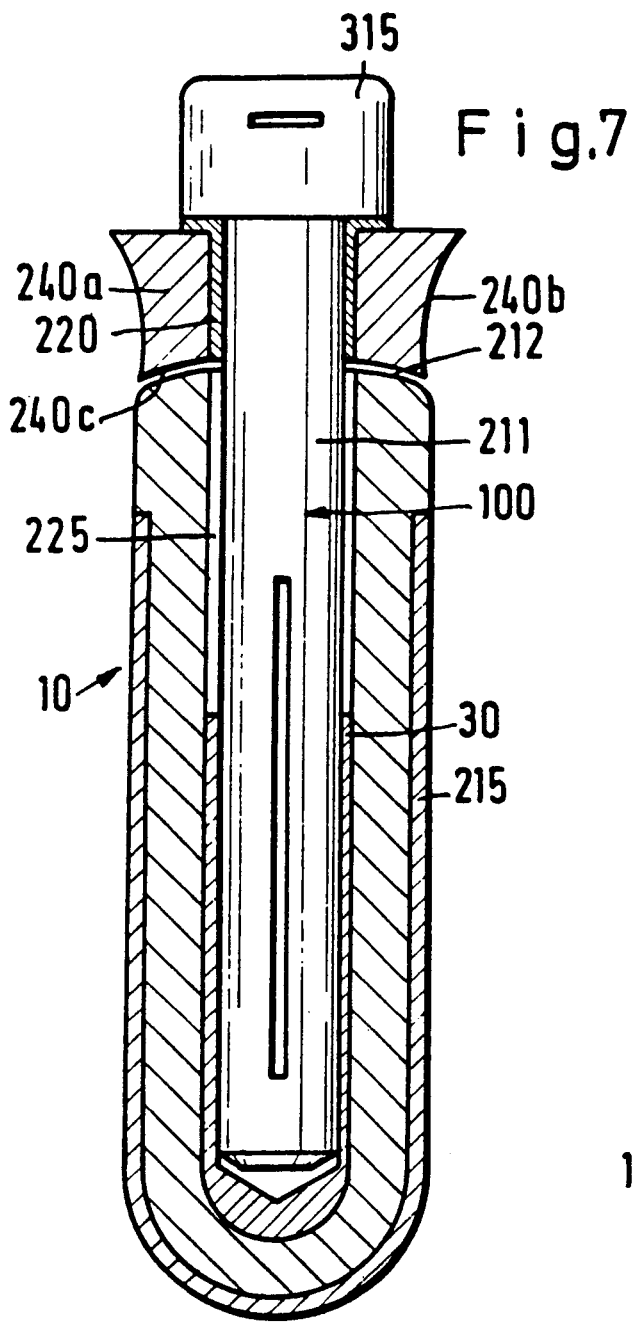
FIG. 7 is partly an elevational and partly a vertical sectional view of another embodiment of an enossal implant with spherical sliding surfaces.
Figure 8:
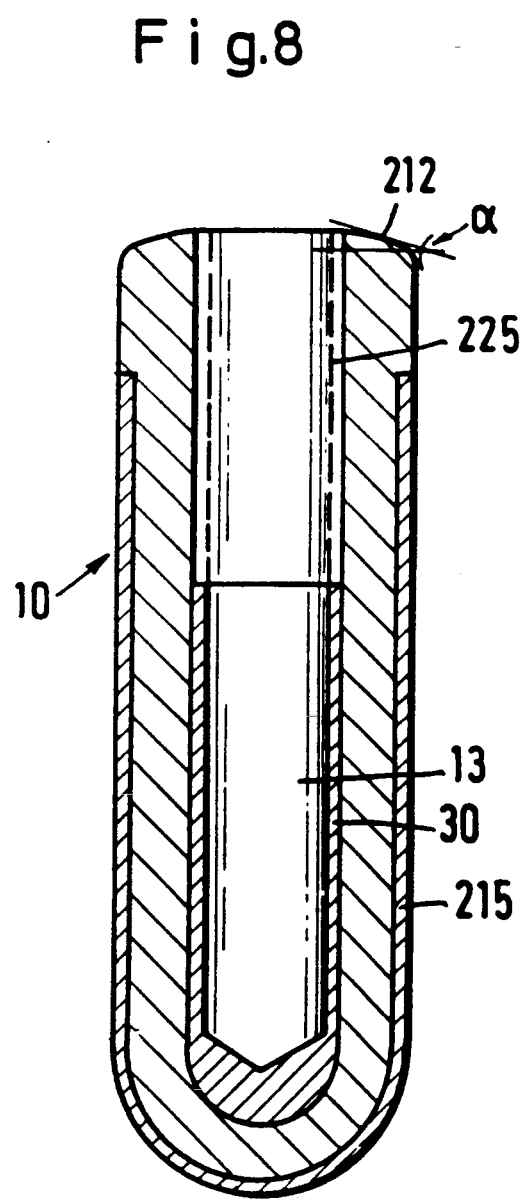
FIG. 8 is a vertical sectional view of the primary cylinder of the implant according to FIG. 7.

While in the implant embodiment of FIGS. 4 and 5 the sliding surface 212 in the upper region of primary cylinder 10 extends at a right angle to the longitudinal axis of cylinder 10 and, therefore, extends horizontally, the sliding surface 212 of primary cylinder 10 for implant attachment 240a according to the embodiment of FIGS. 7 and 8 is constructed as a cup with the angle α of, in particular, 9.27°. In this embodiment, the upper implant attachment 240a (FIG. 9) is constructed as an approximately cylindrically shaped member. The external wall surface 240b of attachment 240a has an arcuate shape and a lower external diameter which corresponds roughly to the external diameter of primary cylinder 10. The upper external diameter of implant attachment 240a is larger than the lower external diameter. In addition, the lower bearing surface 240c of implant attachment 240a is adapted to the sliding surface 212 of primary cylinder 10, so that a completely satisfactory sliding of attachment 240a on cylinder 10 is ensured. Thus, implant attachment 240a is slidingly held on the surface of primary cylinder 10.

Oscillating rod 211 of secondary cylinder 100 is anchored in guide tube 30. The external diameter of oscillating rod 21 is smaller than the internal diameter of longitudinal bore 13 of primary cylinder 10, so that the oscillating rod 211 is held in a firmly seated manner in longitudinal bore 13 of cylinder 10.

In addition the oscillating rod 211 of secondary cylinder 100 is held in primary cylinder 10 by means of a heat seal 250 (FIGS. 4 and 6). Heat seal 250 is located roughly in the center of the primary cylinder 10 or of the guide tube 30 and includes a bimetallic wire 251 (e.g. memory metal) which is held in an annular slot 312 in the oscillating rod 211. In the same way as oscillating rod 211 is held by heat seal 250 in primary cylinder 10, the fitting cap 330 is held on the fitting head 315. Heat seal 350 also comprises a bimetallic wire 351 (e.g. of memory metal), wherein wire 351 is held in an annular slot 316 in fitting head 315 (FIG. 6). As shown in FIG. 6, fitting head 315 tapers conically upwards.

The outer coating 215 on primary cylinder 10 is in particular of hydroxyl-apatite ceramic. As shown in FIG. 8, this outer coating 215 extends over a major portion of the primary cylinder 10. The upper region of the primary cylinder does not have an outer coating. The upper region constitutes the contact zone A which corresponds to the cortical zone, while contact zone B corresponding to the spongiosa carries the outer coating 215.

In order to reduce the torque, horizontal forces transferred to the fitting cap 330 and consequently to the heat 315 of oscillating rod 211 of secondary cylinder 100 lead to the oscillation of rod 211. Thus, a torque is formed. This torque is reduced by means of the oscillating rod in the following way. Implant attachment 240 or 240a slides on the surface 212 of primary cylinder 10 and part of the torque is used up by the resulting sliding friction. In the case of the implant according to FIG. 7, this sliding surface 212 is constructed as a cup and advantageously has an angle α of 9.27°. Since the implant attachment 240 or 240a slides in region 240c on primary cylinder 10, tilting or breaking cannot occur, as would happen in the case of exactly planar surfaces and high surface pressures. The surfaces slide in a moist and not a dry manner on one another. This moisture is ensured by the use of an alumina ceramic, which has the property of making available free oxygen ions on its surface which are automatically combined to form a free lubricating film with substances from the surrounding medium. The material ensures a self-lubrication on the sliding surface in this way and this property of alumina ceramic leads to a high self-lubricating action.

The upper modular tube 220 is made of a highly elastic material and acts as a vibration damper. As a result of this damping, more of the torque is converted to heat. An air gap 225 is located below the upper modular tube 220 so that oscillating rod 211 of the secondary cylinder 100 inserted in primary cylinder 10 can oscillate freely in its oscillating region. The oscillations are converted into heat.

The embodiment shown in FIGS. 7 and 9 has an implant attachment 240a with a different shape as compared to attachment 240. Implant attachment 240a is constructed as a roughly cylindrically shaped member whose outer wall surface 240b has an arcuate shape and whose lower external diameter approximately corresponds to the external diameter of primary cylinder 10, while the upper external diameter is the same or larger than that of the primary cylinder 10.

A guide tube 30 is provided below air gap 225 in the inner area of primary cylinder 10. The guide tube 30 is bonded into the primary cylinder. The oscillating rod 211 of secondary cylinder 100 is anchored with an exact fit in guide tube 30. Heat seal 250 is located on oscillating rod 211 in the upper region of guide tube 30.

Since the oscillating rod is anchored by means of the heat seal and is fitted into guide tube 30, torques not reduced in the aforementioned manner are transferred to the primary cylinder 10 via guide tube 30 throughout the bearing zone of oscillating rod 211. Specifically, the transfer is not in a punctiform manner in the vicinity of heat seal 250. Instead, the torques are distributed over the entire area of guide tube 30. The remaining torques conducted in a distributed manner to the bones are so small that they no longer impair the firm connection of the primary cylinder to the bone which connection is produced through the hydroxylapatite coating 21 of the outer cylinder. This "energy-decreasing" and "bearing-protecting" mechanism makes it possible for the first time to use primary cylinders made from alumina ceramics with a wall thickness of only 0.9 mm and consequently to produce for the first time a late implant with a diameter of only 4 mm made from body-friendly alumina ceramic because, as a result of this torque-reducing mechanism, there is scarcely any mechanical stressing of the primary cylinder 10.

An air layer 320 (FIG. 4) is located between oscillating head 315 of oscillating rod 211 of secondary cylinder 100 (bottom of the cone) and implant attachment 240. Thus, the oscillating rod 211 can oscillate as a result of horizontally acting forces. The rod 211 is damped by the upper modular tube 220 which, when the secondary cylinder 100 is inserted, extends with a portion into the interior of the longitudinal bore 13 of primary cylinder 10. As a result of this construction, modular tube 220 simultaneously provides guidance in primary cylinder 10. The implant attachment 240 slides on the sliding surface which is formed by the bottom of implant attachment 240 and by the top of primary cylinder 10, wherein both surfaces are ground flat and highly polished. In the case of chewing forces acting horizontally on head 315 of oscillating rod 211 or the underlying fitting cap 330, secondary cylinder 100 moves on primary cylinder 10. The horizontal displacement is 150μ, which corresponds to the mobility of the natural parodontium. This mechanism imitates the natural parodontium and is completely maintenance-free.

It is also important that the construction of the implant ensures a high gap sealing action. The implant is actually only made from two parts, namely, primary cylinder 10 and secondary cylinder 100. The heat seal 250 comprises a memory metal wire 251 which is located in annular slot 312 in oscillating rod 211. Due to expansion at body temperature, heat seal 250 anchors oscillating rod 211 and consequently secondary cylinder 100 in primary cylinder 10. Guide tube 30 is provided with a groove for the engagement of the heat seal. In its upper part, this groove forms a sloping plane and in its lower part a circular portion, so that when circumferentially extending memory metal wire 251 expands, secondary cylinder 100 is drawn into primary cylinder 10. Thus, in the vicinity of the sliding surfaces between implant attachment 240 and primary cylinder 10, a gap sealing effect is obtained, which is tight to both bacteria and to moisture.

Guide tube 30 is bonded under a clearly defined pressure in primary cylinder 10. This is achieved by bridging the air gap 320 between oscillating head 315 of oscillating rod 211 and fitting cap 330 and implant attachment 240 by an inelastic disc and placing guide tube 30 in such a way that the heat seal 250 produces the maximum defined tensile strain. The dentist need then only introduce the secondary cylinder 100 under a clearly defined pressure to ensure that the heat seal engages in the groove at the intended point, so that, consequently, the necessary tension and gap sealing effect are ensured. Actual introduction takes place when the patient bites on the fitting cap 330, wherein pressure measuring strips which can be connected to a digital pressure read-off means are used. The aforementioned gap sealing effect is in particular achieved through the use of the two heat seals 250, 350 corresponding to the embodiment of FIG. 4.

Another embodiment of the implant is shown in FIGS. 10 and 11 which in its basic construction corresponds to that of FIG. 7. Modular tube 220 is in this case provided in its upper end region 220a with a projecting disc or ring-like portion 220b which partly overlaps the implant attachment 240 (240a). Portion 220b extends radially over the external diameter of oscillating head 315 into the vicinity of an engagement slot 330a in fitting cap 330 and simultaneously ensures the formation of an air gap 320. It is possible in this way to reliably bond modular tube 220 to implant attachment 240 (240a) and to the oscillating head 315, so that the components are securely joined and simultaneously the air gap 320 is formed (FIG. 1).

FIG. 10 shows a heat seal embodiment differing from other implant heat seal embodiments. For this purpose, the oscillating rod 211 is provided with longitudinal openings 313a, 313b, 313c, 313d which extend parallel to the longitudinal axis of oscillating rod 211 into the interior of a longitudinal through-bore 311a of rod 211. Bimetallic wires, e.g. of memory metal, are inserted through the longitudinal bore 311a into the interior of oscillating rod 211 in such a way that they extend outwards through longitudinal openings 313a, 313b, 313c, 313d and, when secondary cylinder 100 is fitted in primary cylinder 10, are in contact with guide tube 30.

This also ensures that the oscillating rod 211 is reliably held in guide tube 30 in the bearing region. Thus, energy which has not already been converted into heat in the oscillation zone can be transferred to primary cylinder 10 over a large area.

The enossal implant shown in FIGS. 12 to 19 also includes primary cylinder 10 and secondary cylinder 100 and is constructed in accordance with the implant of FIGS. 4 to 11. However, this implant does not have a heat seal 250 in oscillating rod 211. The same parts are provided with the same reference numerals in FIGS. 12 to 19. The secondary cylinder 100 is inserted in primary cylinder 10 prior to the implantation of the complete implant.

In addition, oscillating rod 211 of secondary cylinder 100 is held in the primary cylinder 10 by means of an adhesive.

Specifically, the bottom end of oscillating rod 211 is fixed by an adhesive to guide tube 30. However, it is also possible to construct primary cylinder 10 without a guide tube 30, such that the bottom end of the oscillating rod 211 is directly held on the wall surface of longitudinal bore 13 of primary cylinder 10 by means of the adhesive.

It is also possible to arrange the oscillating rod 211 of secondary cylinder 100 in the center of primary cylinder 10 or of guide tube 30 and to connect the oscillating rod 211 to guide tube 30 or to the wall surface of longitudinal bore 13 of primary cylinder 10 by means of the adhesive, wherein the connecting zone only has to extend over a short portion.

Figure 12:
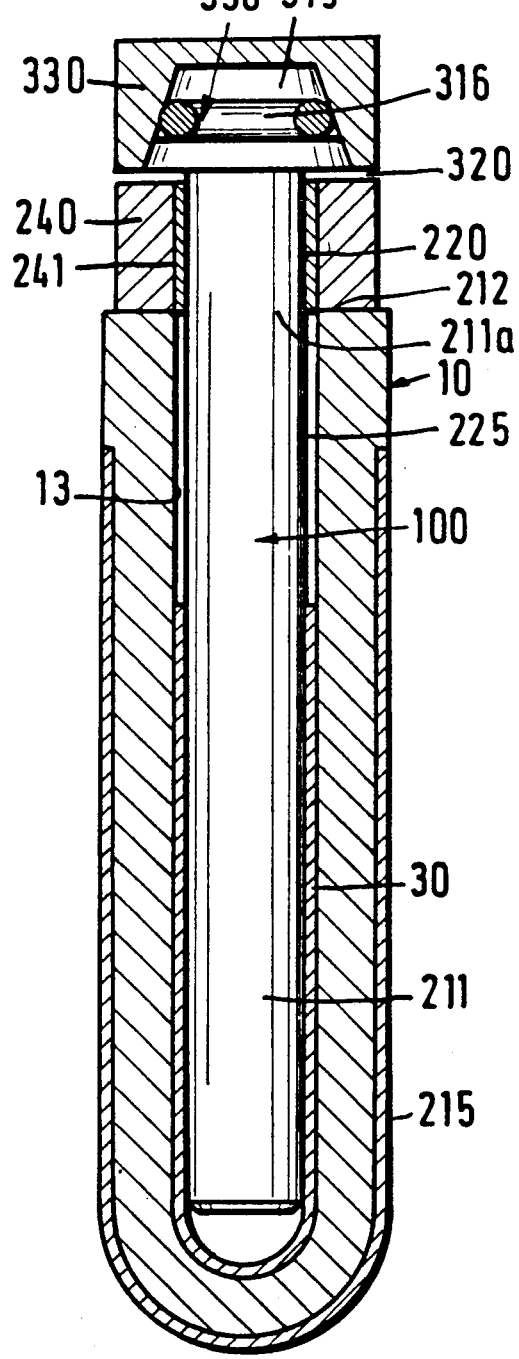
FIG. 12 is partly an elevational and partly a vertical sectional view of another embodiment of an enossal implant comprising a primary cylinder and a secondary cylinder with an oscillating rod bonded into the guide tube.
Figure 13:
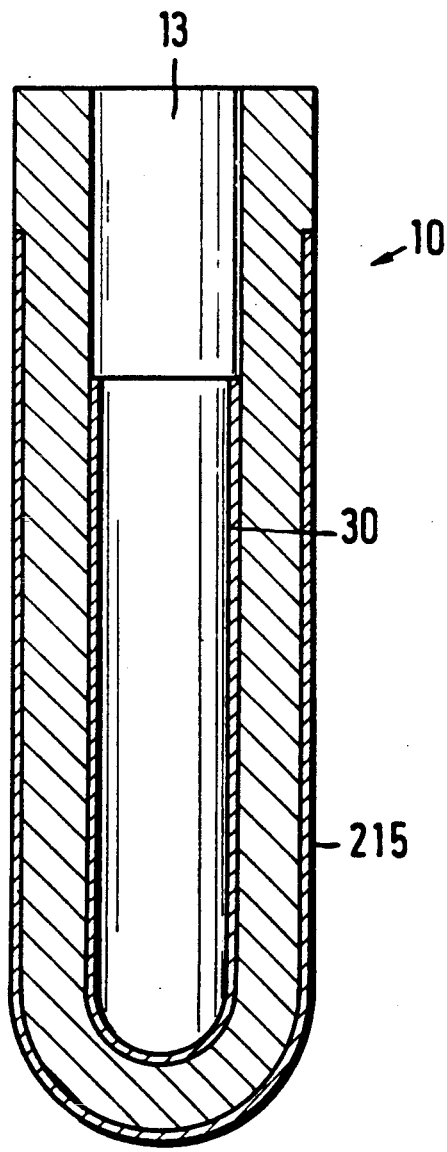
FIG. 13 is a vertical sectional view of the primary cylinder according to FIG. 12.
Figure 18:
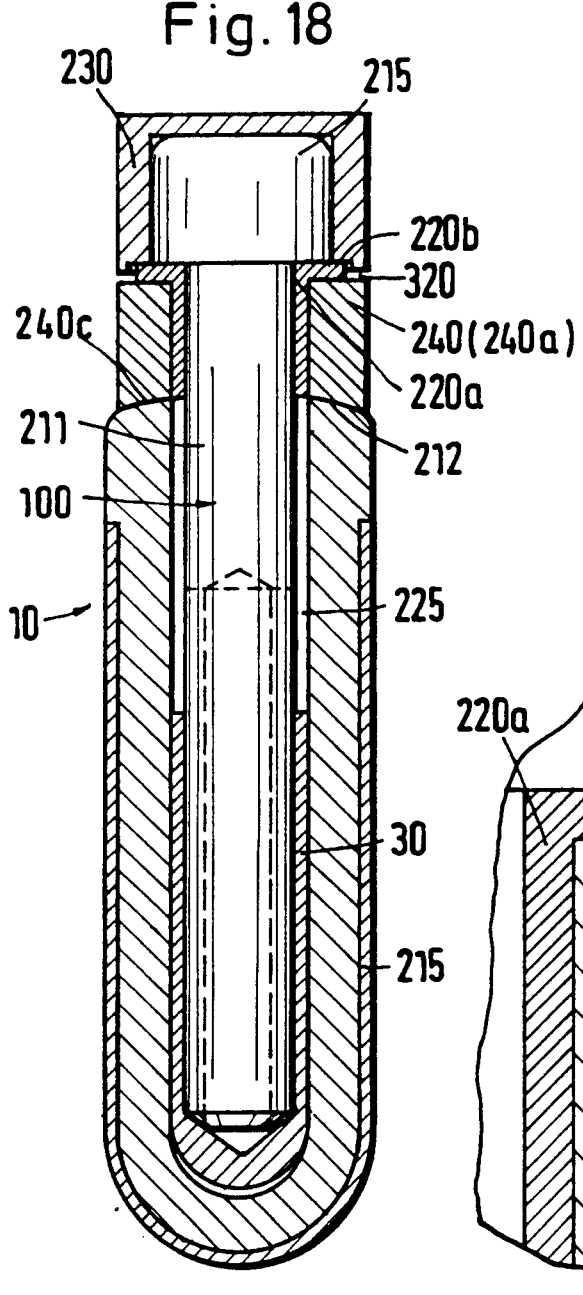
FIG. 18 is partly an elevational and partly a vertical sectional view of another embodiment of an enossal implant with bonded oscillating rod.
Figure 19:
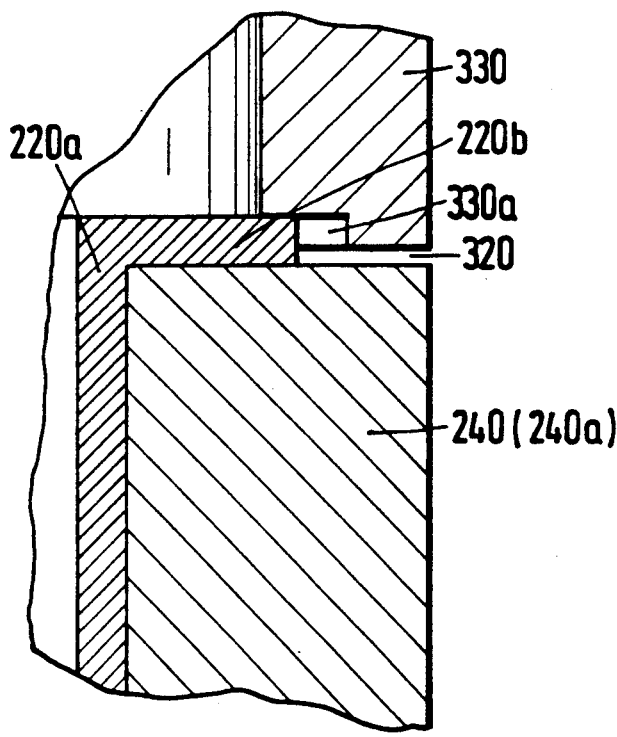
FIG. 19 is a view of a detail of the transition region between the modular tube, implant attachment and secondary cylinder in the embodiment of FIG. 18.

The fitting cap 330 can be fixed to oscillating head 315 by means of a heat seal 350 in FIG. 12. This heat seal 350 is made from a bimetallic wire 351, e.g. of memory metal, which is located in an annular slot 316 in fitting head 315 (FIG. 14). As shown in FIG. 14, the fitting head 315 tapers conically upwards.

Guide tube 30 is located below air gap 225 in the inner area of primary cylinder 10. The tube 30 is bonded into cylinder 10. The oscillating rod 211 of secondary cylinder 100 is anchored with exact fit in guide tube 30 and is also held therein by an adhesive connection, wherein it is also possible that the adhesive connection extends over the entire region of tube 30.

Since oscillating rod 211 is anchored by means of the adhesive connection and is fitted into guide tube 30, torques not reduced in the aforementioned manner in the entire bearing area of oscillating rod 211 are transferred by guide tube 30 to primary cylinder 10 and are distributed over the entire area of tube 30. The torques are not transferred in a punctiform manner in the vicinity of the adhesive connection. The remaining torques supplied in distributed manner to the bones in this way are so small that they no longer impair the firm connection between the primary cylinder and the bones which connection is produced by means of the hydroxyl-apatite coating 215 of the external cylinder of cylinder 10. This "energy-reducing" and "bearing-protecting" mechanism also makes it possible for the first time to use an alumina ceramic primary cylinder with a wall thickness of only 0.9 mm and, consequently, for the first time makes it possible to produce a late implant with a diameter of only 4 mm from a body-friendly alumina ceramic material, because as a result of this torque-reducing mechanism primary cylinder 10 is scarcely mechanically stressed.

Guide tube 30 is bonded under a clearly defined pressure in primary cylinder 10 by bridging the air gap 320 between oscillating head 315 of oscillating rod 211 and fitting cap 330 and implant attachment 240 by an inelastic disc.

According to FIG. 20, the implantation of an implant comprising a primary cylinder and a secondary cylinder takes place in the following way, the individual steps being designated A, B, C and D. The jawbone is denoted by reference numeral 410 and, for simplifying the description, a planar configuration of the jawbone surface is assumed.

The preparation of the bore for receiving implant 200 is called stage A. First, a depression 405 is milled in jawbone 410. The depression has a larger diameter than the actual bore 406 to be made, while its depth is less than the length of implant 400, as can be gathered from FIG. 20. When depression 405 is cut, simultaneously a centering recess is formed which forms the center for a borehole 405 to be made. After producing depression 405, borehole 406 is made. The length of borehole 406 is somewhat less than that of implant 400, so that the connecting attachment 401 of implant 400 comes to rest in depression 405, as represented in stage B in FIG. 20.

Figure 20:
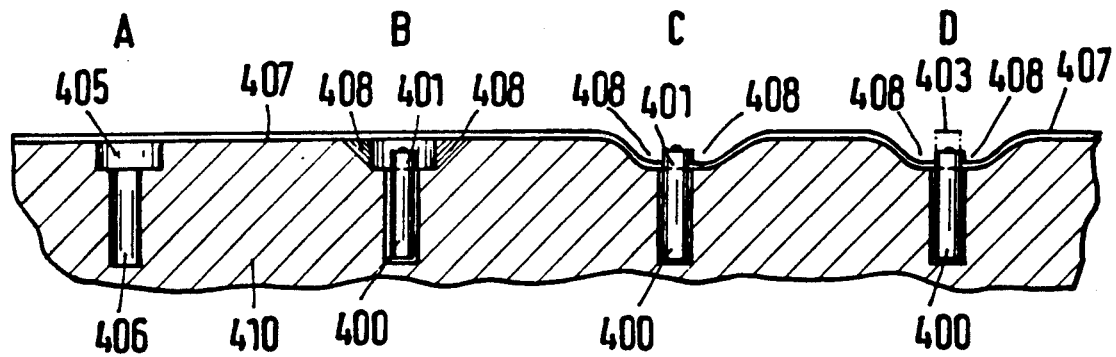
FIG. 20 is a diagrammatic view illustrating the individual process steps of the two-phase implantation process.

After implant 400 is inserted according to stage B, the implant heals in without any load being applied and prior to the occurrence of a bone atrophy, which is indicated by hatched portions 408 in FIG. 20. The mucous membrane 407 closes the depression 405 above implant 400, wherein a portion of the implant 400 extends into depression 405. After incorporation, the connecting attachment can be provided with a cap which fills depression 405 and consequently prevents any new bone formation.

This is followed by bone atrophy. It is a provoked atrophy which is determined by the depth of depression 405 and the length of the implant portion extending into depression 405. After incorporation, the connecting attachment can be provided with a cap which fills depression 405 and consequently prevents any new bone formation.

When the atrophy advances, the mucous membrane 407 adapts to the advancing bone shrinkage and rests against implant 400 in the bottom area of depression 405. After incorporation, the connecting attachment can be provided with a cap which fills depression 405 and consequently prevents any possible new bone formation. When bone atrophy stops, implant 400 with its connecting attachment 401 projects out of mucous membrane 407, as indicated by stage C. The healing phase can be shortened by opening the mucous membrane still covering the implant when atrophy has been completed, so that the implant head is exposed. This is always advantageous if the implant 400 is inserted deep into the jawbone. Subsequently, according to stage D of FIG. 20, the prosthesis mount 403 is fixed, and the prosthesis is mounted and screwed to the mount.

Stages B and C of FIG. 20 represent the first phase of implantation, in which the complete implant is implanted in the borehole formed in the jawbone. This is possible because the secondary cylinder is inserted in and fixed to the primary cylinder. In the second phase, the prosthesis mount is screwed on and, finally, the prosthesis is introduced. The preparation of the depression and of the borehole for inserting the implant can be included in the first phase. FIG. 15 shows the different mucous membrane and jawbone limits when using the old implantation method and the method according to the invention. When using the old method, according to which first the primary cylinder is implanted and then the secondary cylinder is inserted in and connected with the primary cylinder, the mucous membrane limit is indicated at a1 and the bone limit at a2. When using the process according to the invention, the mucous membrane limit and jawbone limit are at b, wherein c represents the bone limit after atrophy.

FIG. 21 shows an implant comprising primary cylinder 10 and secondary cylinder 100 whose oscillating rod 211 is fixed by means of a screw thread 536 in a shaped body 535 in the inner area of the primary cylinder. The shaped body 535 is fixed in the interior of the primary cylinder by means of an adhesive connection 537. In this embodiment, the guide tube is replaced by the shaped body 535. The shaped body 535 is placed in the cavity otherwise taken up by the guide tube, including the gap formed between the bottom end of oscillating rod 211 and the inner base surface of primary cylinder 10. The shaped body 535 has a top bore which is provided with an internal thread. The external thread at the end of the oscillating rod 211 engages in the internal thread, so that the screw connection 536 can be made after inserting oscillating rod 211 into shaped body 535. Otherwise the implant is constructed in accordance with the embodiment of FIG. 18 and is provided with implant attachment 240 or 240a an oscillating head 315 which is surrounded by the fitting cap 330. The upper region of the oscillating rod 211 is supported on the inner wall surface of modular tube 220.

In the aforementioned examples, primary cylinder 10 and secondary cylinder 100 are made of ceramic materials. The primary cylinder is introduced through the cortical zone into the spongiosa, wherein the primary stability is achieved by positive engagement between the implant and the implant bed, on the one hand, and by frictional engagement of bone tissue attached to the alumina ceramic surface of the primary cylinder, on the other hand.

In place of heat seals or other fastening systems for the oscillating rod 211 in primary cylinder 10, it is also possible to use detachable or undetachable clamp fasteners, as shown in FIGS. 22 to 31. In the case of the embodiment shown in FIG. 22, the oscillating rod 211 of secondary cylinder 100 is held in primary cylinder 10 by a detachable clamp fastener. For this reason, the guide tube 30 held in primary cylinder 10 in its base region by means of an adhesive has a short length. In the interior of guide tube 30 is arranged a shaped or molded member 600 which is a solid cylinder and is made of a metal or some other suitable material which can be fixed by an adhesive to guide tube 30. This shaped member 600 advantageously has a length corresponding to that of guide tube 30.

Shaped member 600 is provided on its side 601 facing modular tube 220 with a spherical or some other geometrically shaped mount 602 which is surrounded by a capsule-like element 603 which, in turn is integrally formed with the bottom end of oscillating rod 211. Shaped member 600 is constructed in one piece with its mount 602. In the same way, element 603 is constructed at the bottom end of oscillating rod 211 and is secured thereto.

This capsule-like element 603 on oscillating rod 211 has on its inner wall surface 603a facing mount 602 a bimetallic strip 604 which may be of memory metal. This bimetallic strip 604 may be incorporated into the material of the capsule-like element 603. However, it is also possible for the bimetallic strip 604 to be arranged in the form of an inner coating or insert on the inner wall surface of element 603. The complete mount 602 can also be made of memory metal.

The capsule-like element 603 is mounted on the spherical mount 601 with the bimetallic strip or memory metal being in the cooled state, so that, the capsule-like element 603 surrounds the spherical mount 602 after warming or heating of the strip. As a result, the oscillating rod 211 of secondary cylinder 100 inserted in primary cylinder 10 is held firmly on shaped member 600, but it is possible because of the clamping connection to remove secondary cylinder 100 from primary cylinder 10. Mount 602 can also be made from a resilient elastic material.

According to FIGS. 23 to 26, the oscillating rod 211 of secondary cylinder 100 in primary cylinder 1 and the fitting head 330 on oscillating rod 211 are secured by means of a clamp fastener made of a memory metal. These two clamp fasteners are shown at 630 and 630a in FIG. 23. In this embodiment of the enossal implant, no guide tube 30 is provided in the longitudinal bore of primary cylinder 10. In the bottom region of primary cylinder 10, shaped member 600 is inserted in the longitudinal bore of primary cylinder 10 and is connected to the inner wall surface of the primary cylinder 10 by an adhesive. The spherical mount 602 is mounted in upper region of the shaped member 600. The spherical mount 602 is surrounded by the capsule-like, memory metal element 603 which is fixed to the lower end of oscillating rod 211. Clamp fastener 630a is constructed in the same way as fastener 630 and secures fitting head 330 on oscillating rod 211 (FIGS. 23, 24 and 26). The clamp fastener 630 is formed by the spherical mount 602a which is mounted on the upper end of oscillating rod 211. The oppositely arranged element, i.e., the capsule-like memory metal element 603a is mounted in the fitting head 330 (FIG. 26). FIG. 26 shows the capsule-like element 603a before being deformed for engagement.

According to another embodiment, instead of bimetallic strip 604, the capsule-like element 603 may be provided on its inner wall surface with a coating, an insert or the like made of a permanent elastic material, such as, a polyurethane elastomer or other suitable elastic material. The use of a bimetallic strip ensures that the secondary cylinder 100 is drawn against the primary cylinder 10, so that when the bimetallic strip expands the friction of the spherical sliding surfaces of secondary cylinder 100 and implant attachment 240 can be controlled. In all other respects, the construction of the implant according to FIG. 22 corresponds to that of the implant of FIG. 7. Guide tube 30 need not have the short length shown in FIG. 22. It is also possible to provide guide tube 30 with the length shown in FIG. 7, wherein the shaped member 600 is fixed by an adhesive in the bottom region of guide tube 30 and may have a shorter length than member 600.

In the embodiment of FIGS. 27 to 30, the oscillating rod 211 is held in primary cylinder 10 by means of an undetachable clamp fastener 640. For this purpose, guide tube 30 whose lower region is fixed in primary cylinder 10 by means of an adhesive is constructed in its bottom region as a solid cylinder. The resulting shaped or molded member is designated 610 and is made of a metal or other suitable material. The shaped member 610 forms with the guide tube 30 a unit, wherein the length of shaped member 610 represents about half the total length of shaped member 610 with guide tube 30.

The shaped member 610 formed in the upper region and serving as guide tube 30 is provided with a top bore 611. At least one annular slot 612 is provided in the vicinity of the inner wall surface 611a of the bore. Slot 612 is directed radially and may have a triangular cross-section. The oscillating rod 211 has a plurality of bead-like rings 613 on the outer periphery of its bottom end which is constructed as a pin 211a. Rings 613 engage in the annular slot 612 when oscillating rod 211 is inserted in bore 611 of shaped member annular slots 612 in bore 611 of shaped member 610. The number of annular slots 612 in bore 611 of shaped member 610 can be selected at random. One annular slot 612 is sufficient for a firm seat of oscillating rod 211 in primary cylinder 10 (FIGS. 27, 28 and 29).

In the same way as oscillating rod 211 of secondary cylinder 100 is held in primary cylinder 10 using shaped member 610, it is also possible to fix fitting head 330 on the free upper end of oscillating rod 211, wherein a portion of the upper end of oscillating rod 211 projects out of the implant attachment 240. The clamp fastener for the fitting cap 330 is designated 640a and is constructed in accordance with the clamp fastener 640 (FIG. 27). The fitting cap 330 is provided with a bore 711b which has an annular slot 612a on the inner wall (FIG. 30). The upper free end of oscillating rod 211 is constructed in such a way that it can be inserted in bore 611b. Oscillating rod 211 carries at its upper outer periphery a ring-like bead 613a which is profiled in such a way that, after mounting fitting cap 330 on oscillating rod 211, bead 613a engages in the annular slot 612a in fitting head 330 (FIG. 29). By inserting the individual parts and applying a slight pressure, the clamp fasteners 640, 640a are formed (FIG. 27).

FIG. 31 shows two different embodiments of a clamp fastener A, B. In embodiment A, concentric annular slots 612 are provided, while oscillating rod 211 carries concentric, bead-like rings 613 on its outer circumference. Rings 613 are constructed and arranged in such a way that, after inserting oscillating rod 211 in primary cylinder 10, the rings 613 engage in the annular slots 612.

In the case of the embodiment indicated at B, annular slots 612 or the annular slots of bore 611 of shaped member 610 have an approximately triangular cross-section for forming upper undercuts 614, while the oscillating rod 211 is provided on its outer bottom circumference with a plurality of ring-like engagement profiled 615 corresponding to the number of annular slots 612, so that, after inserting the bottom end of rod 211 in bore 611 of shaped member 610, the engagement profiles 615 engage in slots 612, so that it is not possible to detach or release the clamp fastener.

The gap sealing effect between the two spherical sliding surfaces 212, 240c of primary cylinder 10 and implant attachment 240 and 240a is achieved as a result of the exactly fitting and positive bearing engagement of the spherical sliding surfaces of the primary cylinder 10 and the implant attachment or the mucous membrane sleeve forming the ceramic upper part, and as a result of chemisorption which is caused by the ceramic material used. Chemisorption occurs because the ceramic material gives off oxygen ions at its surface and the ions are combined with the surrounding medium to form a sliding coating. Atmospheric humidity is normally sufficient to bring about chemisorption. Thus, a sliding or lubricating film is formed by utilizing properties of the material.

It is also possible to achieve a gap sealing effect with a coating 620 or an insert of polytetrafluoroethylene, known under the tradename of Teflon, or other suitable material, particularly oxygen ion-permeable material, as shown in FIG. 32. The coating materials to be used in particular are those which do not impair chemisorption. The coating can be replaced by shaped bodies in the form of inserts made from suitable materials. The coating made from these materials can be applied to one of the two spherical sliding surfaces 212 or 240c.

As shown in FIG. 32, air gap 225 between guide tube 30 and the upper modular tube 220 provided in the embodiments described above can be filled by another modular tube 30a placed above the guide tube 30. The modular tube 30a may be of permanent elastic material such as plastic material or other suitable material. This additional modular tube 30a ensures an adequate gap sealing effect.

The upper circumferential edge of modular tube 220 is bent outwards in sleeve-like manner. This bent or angular portion is designated 220c and is used for compensating the rod compression when vertical forces occur (FIGS. 27 and 29).

I claim:

1. Enossal implant for the securing of a fixed or removable dental prosthesis, comprising two interconnectable parts, whereof one part is constructed as a primary cylinder (10) with a bottom and a central longitudinal bore (13), wherein the primary cylinder can be introduced into the jawbone and anchored therein and the other part is constructed as a secondary cylinder (100) with an implant post (150) which can be introduced into the longitudinal bore of the primary cylinder and is held therein, a tubular intermediate member mounted between the primary cylinder and the secondary cylinder, said implant post being constructed at its free upper end for the connection of the dental prosthesis, the implant post (150) of the secondary cylinder (100) being a lever member in the longitudinal bore (13) of the primary cylinder and being surrounded by a force line system for diverting the horizontal, vertical, torsional or any combination of the three forces occurring in the vicinity of the dental prosthesis or mouth into the lower region of the secondary cylinder (100) and from there into the bottom of the primary cylinder (10), said system comprising an elastic modular member such that the lever fulcrum of the lever member is located in the lower third of the primary cylinder, the elastic modular member being constructed as a guide tube, the guide tube mounted in the bottom of the cylinder, a modular member-free section being defined adjacent the guide tube when the secondary cylinder (100) is inserted, the modular member-free section forming an air gap, the guide tube and the modular member-free section together having a length which corresponds to the length of the central longitudinal bore (13) of the primary cylinder (10), an upper modular tube (220) being mounted adjacent the modular member-free section, an implant attachment surrounding the upper modular tube.

2. Enossal implant according to claim 1, wherein the implant post of the secondary cylinder (100) is constructed as an oscillating rod (211), on said oscillating rod (211) is arranged the upper modular tube (220) made from highly elastic material and connected by an adhesive joint to rod (211), an implant attachment (240, 240a) having a central through-bore (241) being aligned with the longitudinal bore (13) of primary cylinder (10) and being slidingly held on the surface of primary cylinder (10), the oscillating rod (211) of secondary cylinder (100) being held in guide tube (30) by a heat seal (250) arranged on rod (211) with secondary cylinder (100) inserted in the vicinity of guide tube (30).

3. Enossal implant according to claim 2, wherein oscillating rod (211) is provided at its upper end with a widened portion (315) forming an oscillating head and an air layer is formed between oscillating head (315) of oscillating rod (211) and implant attachment (240, 240a).

4. Enossal implant according to claim 3, wherein the upper modular tube (220) is arranged in the interior of the through-bore (241) of the implant attachment (240, 240a) held in sliding manner on primary cylinder (10) and is held on tube (220) by means of an adhesive joint.

5. Enossal implant according to claim 4, wherein the upper modular tube (220) is provided on its upper end region (220a) with a projecting, disc-shaped portion (220b) and the modular tube (220) is held in the vicinity of portion (220b) by means of an adhesive joint on implant attachment (240, 240a) and on the oscillating head (315) of oscillating rod (211).

6. Enossal implant according to claim 2, wherein the heat seal (250) comprises a bimetallic wire (251) of memory metal the rod (211) having an annular slot (312), the heat seal (150) being held in the annular lot (312) on oscillating rod (211).

7. Enossal implant according to claim 2, wherein the heat seal (250) comprises at least one bimetallic wire (251), arranged in longitudinal openings (313a, 131b, 313c, 313d) extending into the interior of a longitudinal through-bore (311a) of oscillating rod (211).

8. Enossal implant according to one of the claims 2 to 7, wherein the sliding surface (212) of primary cylinder (10) for the implant attachment (240, 240a) is constructed as a cup with an angle α of 9.27°.

9. Enossal implant according to claim 2, wherein the implant attachment (240a) is constructed as a roughly cylindrical shaped member, whose outer wall surface (240b) is drawn in in arcuate manner and whose lower external diameter approximately corresponds to the external diameter of primary cylinder (10), whereby the upper external diameter of implant attachment (240a) is the same or larger than the lower external diameter, wherein the lower bearing surface (240c) is shaped to correspond with the sliding surface (212) of primary cylinder (10).

10. Enossal implant according to claim 2, wherein the contact zone (A) of primary cylinder (10) facing the cortical zone is free from an external coating, and a contact zone (B) of primary cylinder (10) facing the spongiosa carries an external coating (215).

11. Enossal implant according to claim 1, wherein the upper modular tube (220) made from a highly elastic material is joined by an adhesive to the oscillating rod (211) of the secondary cylinder (100), wherein on the modular tube (220) is arranged the implant attachment (240, 240a) with a central through-bore (241) aligned with the longitudinal bore (13) of primary cylinder (10) and which is slidingly held on the surface of the latter, and wherein the oscillating rod (211) of secondary cylinder (100) is fixed in its lower region by means of an adhesive to guide the tube (30).

12. Enossal implant according to claim 11, wherein the upper end of the oscillating rod (211) has an oscillating head (315) and that between the oscillating head (315) of oscillating rod (211) and implant attachment (240, 240a) is formed an air gap (320).

13. Enossal implant according to claim 11, wherein the upper modular tube (220) is arranged in the interior of the through-bore (241) of the implant attachment (240, 240a) slidingly held on the primary cylinder (10) and is held by means of an adhesive on the modular tube (220).

14. Enossal implant according to claim 11, wherein the upper modular tube (220) is provided in its upper end region (220a) with a projecting, disc-shaped portion (220b) and the modular tube (220) is held in the vicinity of portion (220b) on implant attachment (240, 240a) and on the oscillating head (315) of oscillating rod (211) by means of an adhesive.

15. Enossal implant according to claim 11, wherein the heat seal (250) comprises at least one bimetallic wire (251) arranged in a longitudinal through-bore (313a, 313b, 313c, 313d) extending into the interior of a longitudinal through-bore (311a) of the oscillating rod (211).

16. Enossal implant according to claim 11, wherein the sliding surface (212) of primary cylinder (10) for implant attachment (240, 240a) is constructed as a cup with an angle α of 9.27°.

17. Enossal implant according to claim 11, wherein the implant attachment (240a) is constructed as a roughly cylindrical shaped member, whose outer wall surface (240b) extends in an arcuate manner and whose lower external diameter corresponds roughly to the external diameter of the primary cylinder (10), whereby the external diameter of the implant attachment (240a) is the same or larger than the lower external diameter, and wherein the lower bearing surface (240c) is shaped in accordance with the shape of the sliding surface (212) of the primary cylinder (10).

18. Enossal implant according to claim 11, wherein the primary cylinder (10) has an outer coating (215).

19. Enossal implant according to claim 18, wherein the contact zone (A) of primary cylinder (10) facing the cortical zone is free from an outer coating, whereas the contact zone (B) of primary cylinder (10) facing the spongiosa carries the outer coating (215).

20. Enossal implant according to claim 11, wherein the guide sleeve (30) of primary cylinder (10) is eliminated and the oscillating rod (211) with its bottom end region is fixed to the wall of longitudinal bore (13) of primary cylinder (10) by means of an adhesive.

21. Enossal implant according to claim 20, wherein even when omitting the guide tube (30), the oscillating rod (211) is connected by means of a screw connection (536) to a shaped member (535) having an upper bore for receiving rod (211) held by means of an adhesive (537) in the interior of primary cylinder (10), which takes up the entire space of the said guide tube including the space located below it between the bottom end of the otherwise provided guide tube (30) and the primary cylinder bottom.

22. Enossal implant according to claim 2, wherein the primary cylinder (10) is made from a ceramic material or titanium and is externally coated with a hydroxylapatite (11, 215).

23. Enossal implant according to claim 2, wherein the oscillating rod (211) of the secondary cylinder (100) is held in the primary cylinder (10) by means of a clamp fastener (630), which comprises a molded member (600) arranged in the longitudinal bore (13) of primary cylinder (10) having an upper mount (602) and a capsule-like element (602) made from a bimetal arranged at the bottom end of oscillating rod (211) and which engages in clamping manner around mount (602).

24. Enossal implant according to claim 23, wherein the guide tube (30) mounted in the bottom region of the primary cylinder (10) by means of an adhesive has a length substantially shorter than the primary cylinder (10) and in its interior carries a molded member (600), constructed as a solid cylinder and made from a metal which is fixed by means of an adhesive to guide tube (30) and has a length corresponding to the length of guide tube (30) and that the molded member (600) is provided on its side (601) facing the modular tube (220) with a spherical mount (602) which is embraced by a capsule-like element (603), which is shaped onto the oscillating rod (211) at the bottom end thereof and whose wall surface (603a) facing mount (602) carries and insert.

25. Enossal implant according to claim 23, wherein by means of an adhesive a molded member (600) is secured in the bottom region of longitudinal bore (13) and at the top is provided with a spherical mount (602) which is embraced by a capsule-like element (603), which is secured to the bottom end of oscillating rod (211) and is made from a bimetal.

26. Enossal implant according to claim 25, wherein the fitting head (330) is fixed to a clamp fastener (630a), on the oscillating rod (211) of secondary cylinder (100), the upper end of oscillating rod (211) being provided with a spherical mount (602a) and the fitting head (330) being provided in its interior with a claw-like element (603a) which embraces mount (602a) and is made from a bimetal.

27. Enossal implant according to claim 2, wherein the oscillating rod (211) of secondary cylinder (100) is held in primary cylinder (10) by means of a clamp fastener (640), which comprises a molded member (610) arranged in the longitudinal bore (13) of primary cylinder (10) having a central bore (611) provided with an internal annular slot (612) and an annular bead (613) shaped onto the outer circumference of the bottom end of oscillating rod (211) and engaging in annular slot (612) when oscillating rod (211) is inserted in primary cylinder (10).

28. Enossal implant according to claim 27, wherein the annular slot (612) or slots of bore (611) of molded member (610) has a cross-section corresponding to a right-angle triangle for forming undercuts (614) and the oscillating rod (211) is provided on its bottom outer circumference with a number of annular engagement profiles (615) corresponding to the number of annular slots (612) for forming an undetachable clamp fastener.

29. Enossal implant according to claim 27, wherein the molded member (610) is constructed in solid wall manner and carries on its side facing the modular tube (220) a guide tube (30), the molded member (610) is of roughly the same length as guide tube (30), between guide tube (30) and modular tube (220) is formed an air gap (225), and wherein the molded member (610) is provided with an upper bore (611), in whose inner wall surface (611a) is formed at least one annular slot (612) and that at its lower end oscillating rod (611) is formed in pin-like manner and is provided on its outer circumference with at least one annular bead (613) engageable in the annular slots (612) corresponding to the number of the latter, the internal diameter of bore (611) in molded member (610) being smaller than the external diameter of oscillating rod (211) and the external diameter of the oscillating rod pin (211a) corresponding to the internal diameter of bore (611).

30. Enossal implant according to claim 27, wherein the fitting head (330) is fixed to the oscillating rod (211) of secondary cylinder (100) by a clamp fastener (640a), the oscillating rod (211) carrying on the outer circumference of its upper free end an annular bead (613a), which engages in an annular slot (612a) in the inner wall surface of a bore (611b) formed in fitting head (330).

31. Enossal implant according to claim 30, wherein for forming a gap sealing effect between the two spherical sliding surfaces (212, 240c) of the primary cylinder (10) and the implant attachment (240, 240a), at least one of the two sliding surfaces is provided with a coating (620) made from polytetrafluoroethylene.

32. Enossal implant according to claim 31, wherein the air gap (225) between guide tube (30) and the upper modular tube (220) is filled by a modular tube (30) made from elastic material mounted above the guide tube (30).

33. Enossal implant according to claim 32, wherein the upper circumferential edge of the modular tube (220) is bent outwardly in sleeve-like manner.

34. Enossal implant according to claim 6, wherein the bimetallic wire (251) is of memory metal.

35. Enossal implant according to claim 7, wherein the at least one bimetallic wire (251) is of memory metal.

36. Enossal implant according to claim 15, wherein the at least one bimetallic wire is (251) is of memory metal.

37. Enossal implant according to claim 36, wherein the outer coating is of hydroxyl-apatite ceramic.

38. Enossal implant according to claim 23, wherein the capsule-like element (602) is made of memory metal.

39. Enossal implant according to claim 24, wherein the insert is a bimetallic strip.

40. Enossal implant according to claim 39, wherein the bimetallic strip is of memory metal.

41. Enossal implant according to claim 24, wherein the insert is made from an elastic material.

42. Enossal implant according to claim 25, wherein the capsule-like element 603 is made of memory metal.

43. Enossal implant according to claim 26, wherein the claw-like element (603a) is made of memory metal.

44. Enossal implant according to claim 31, wherein the coating (620) is made of oxygen ion-permeable material.

* * * * *

UNITED STATES PATENT AND TRADEMARK OFFICE
CERTIFICATE OF CORRECTION

PATENT NO. : 5,061,285
DATED : October 29, 1991
INVENTOR(S) : Werner-Lutz Koch It is certified that error appears in the above-identified patent and that said Letters Patent is hereby corrected as shown below: On the title page:

[73] Assignee: Implanto-Lock Gesellschaft mit
beschränkter Haftung für
Implantatforschung-und Entwicklung
of Hamburg, Federal Republic or Germany Signed and Sealed this First Day of June, 1993

Attest:

MICHAEL K. KIRK

Attesting Officer   Acting Commissioner of Patents and Trademarks